US008394979B2

(12) United States Patent
Englert et al.

(10) Patent No.: US 8,394,979 B2
(45) Date of Patent: Mar. 12, 2013

(54) PROCESS FOR PREPARING CYCLOPLATINATED PLATINUM COMPLEXES, PLATINUM COMPLEXES PREPARED BY THIS PROCESS AND THE USE THEREOF

(75) Inventors: Ullrich Englert, Herzogenrath (DE); Anca Beatrice Braun, Aachen (DE)

(73) Assignee: Rheinische-Westfalische Technische Hochschule Aachen, Aachen (DE)

( * ) Notice: Subject to any disclaimer, the term of this patent is extended or adjusted under 35 U.S.C. 154(b) by 351 days.

(21) Appl. No.: 12/747,774

(22) PCT Filed: Dec. 12, 2008

(86) PCT No.: PCT/EP2008/067452
§ 371 (c)(1),
(2), (4) Date: Jun. 11, 2010

(87) PCT Pub. No.: WO2009/077462
PCT Pub. Date: Jun. 25, 2009

(65) Prior Publication Data
US 2010/0267977 A1    Oct. 21, 2010

(30) Foreign Application Priority Data
Dec. 14, 2007  (DE) ................. 10 2007 060 918

(51) Int. Cl.
*C07F 15/00*      (2006.01)
*A61K 31/28*      (2006.01)
(52) U.S. Cl. ........................ 556/137; 514/492
(58) Field of Classification Search .............. 556/137; 514/492
See application file for complete search history.

(56) References Cited

FOREIGN PATENT DOCUMENTS

| GB | 2 134 103 A | 8/1984 |
|----|-------------|--------|
| GB | 2 209 161   | 5/1989 |
| WO | 01/36431 A  | 5/2001 |

OTHER PUBLICATIONS

Avshu et al, The Preparation of cis- and trans- (PT (amine) 2 (CN) 2 complexes, and some observations on the rectivity of platinum (II) cyanide obtained by different rourtes. Chemical Abstract, Acc. No. 1985:88935.
Bednarski et al, "Aqueous Chemistry of mixed-amine cis-and transplatin analogues. Intramolecular preference for a kinetic six-membered ring over a thermodynamic five-membered ring ortho-platination product" Inorganic Chemistry, 1991, 30, 15, S.3015-3025.
Capape et al, "A comparative study of the 0structures and reactivity of cyclometallated platinum compounds of N-benzylidenebenzylamines and cycloplatination of a primary amine" Dalton Trans. May 28, 2007;(20):2030-9. Epub Mar. 23, 2007.
Carlone et al, "Role of metal ions and hydrogen bond acceptors in the tautomeric equilibrium of nitro-9 [(alkylamino) amino]—acridine drugs" Chemical Abstract, Acc. No. 2004:518965.
Ceci et al, "Coordination and peri-Carbon Metalation of 1-Nitro-9-(2-aminoethyl) amino) acridines toward Platinum (II). Evidences for Hydrogen bonding between Endocyclic N (10) H and Chloride Ion" Inorganic Chemistry, 1996, 35, 4, S.876-82, CA, Acc. No. 1996:62488.
Coluccia et al. "Mutagenic activity of some platinum complexes: chemical properties and biological activity" Chemical Abstract, Acc. No. 1984:543548.
Gust et al. "Synthesis and studies on the estrogenic activity of cis- and trans; Bis (2, 6-dichioro-4-hydroxybenzlamine)] dihaloplaatinum (II)-Complexes" Arch. Pharm., 1994, 327, S.763-769.
Casas et al, Pentafluorophenylplatinum Complexes containing $\eta^2$-aryl-Pt Interactions. Crystal Structure of cis-[Pt $(C_6F_5)_2$-$(NC_5H_4[CH(\eta^2-Ph]-2-_\kappa/V)]$ $0.5C_6H_5Me$: J. Chem. Soc. Dalton Trans. 1995, S2949-2954 S.2950.
Haroutounian, "The Use of Strecker Reaction for the Synthesis of Sympathomimetic Amine Analogues and their *cis*-Pt (II) Complexes" Eur. J. Med. Chem. 1987, 22, S.325-329.
Krylova et al. "Diasteromers of trans isomers of PT (II) Complexes with Alanine and Phenylalanine Zhurnal Neorganicheskois" Khimii, 2003, 48, (11), S.1790-1800. Coden: Znokaq. Chemical Abstract Acc. No. 2004:27494.
Krylova et al. "Effect of Solvent on the Cyclization Kinetics of Amino Acids in Platinum (II) Complexes" Chemical Abstract Acc. No. 1976:567252.
Krylova et al. Kinetics of Orthometalation of Phenylalaine Platinum (II) Complexes, Koordinationnaya Khimiya, 1986, 12(12), S.1691-1996. Chemical Abstract, Acc. No. 1988:406696.
Kyrlova et al. Ortho-Metalated Platinum (II) Complexes with Glycine and Phenylalanine. Zhurnal Neorganicheskoi Khimii, 2003:688499.
Mylonas et al. Platinum (II) and Palladium (II) Complexes with Amino Acid Derivatives. Synthesis, Interpretation of IR and Proton NMR Spectra and Conformational Implications. Chemical Abstract, Acc No. 1981:453990.
Rochon et al. "Study of PT (II)-Aromatic Amines Complexes of the Types *cis*- and trans-Pt (amine) 212, (Pt (Amine) 4) 12 and I (amine) Pt. (µ-I) 2Pt (amine) I" Chemical Abstract, Acc. No. 2007:46870.
Tang et al, "Syntheses and Configuration of Haloethyl α-amino acid ester-platinum complexes" Chemical Abstract Acc. No. 1983:514877.
Vogels et al, "Reactions of Aminoboron Compounds with Palladium and Platinum Complexes" Chemical Abstract, Acc. No. 1999:512017.
Avshu, Andre, et al., "Reaction of Silver Ion with [ML2X2] (L-amine or phosphine; M-palladium or platinum; X-iodide, chloride, or thiocycnate) leading to orthometalation and catalytic activity x-ray structure of ab-(2-aminomethyl) phenyl-c-carbonyl-d-iodo platinum(II)", Journal of the Chemical Society, Dalton Transactions, Royal Society of Chemistry, No. 8, Jan. 1, 1972, pp. 1619-1624.
Calmuschi-Cula, Beatrice, et al., "Orthoplatination of Primary Amines", Organometallics, ACS, Washington, CD, US, vol. 27, No. 13, May 23, 2008, pp. 3124-3130.

*Primary Examiner* — Porfirio Nazario Gonzalez
(74) *Attorney, Agent, or Firm* — Occhiuti Rohlicek & Tsao LLP

(57) ABSTRACT

The present invention relates to a process for preparing cycloplatinated platinum(II) complexes, platinum(II) complexes prepared by this process and the use thereof for the treatment of tumor diseases and/or hemo blastoses.

18 Claims, No Drawings

US 8,394,979 B2

PROCESS FOR PREPARING CYCLOPLATINATED PLATINUM COMPLEXES, PLATINUM COMPLEXES PREPARED BY THIS PROCESS AND THE USE THEREOF

CROSS-REFERENCE TO RELATED APPLICATIONS

This application is the National Stage of International Application No. PCT/EP2008/067452, filed on Dec. 12, 2008, which claims the benefit of German Application Serial No. 10 2007 060 918.5, filed on Dec. 14, 2007, the contents of both of the foregoing applications are hereby incorporated by reference in their entirety.

The present invention relates to a process for preparing cycloplatinated platinum complexes, platinum complexes prepared by this process and the use thereof for the treatment of tumor diseases and/or hemo blastoses.

Cisplatin cis-[PtCl$_2$(NH$_3$)$_2$] is one of the top-selling cancer drugs. However, since platinum-based cytostatics exhibit strong side effects and can therefore not be used for the treatment of some kinds of cancer, new compounds overcoming these disadvantages, are continuously investigated. Previous studies of the interaction between molecule structure and anti-tumor activity suggest that complexes for cancer therapy must have a cis-configuration, be uncharged, have an easy exchangeable leaving group and have at least one nitrogen-bound hydrogen atom. However, these narrow rules were broadened by more recent studies showing that also complexes having a trans-configuration or rather charged complexes exhibit anti-tumor activity. Therefore, current cancer research is not longer limited to compounds following the pre-assigned rules, but is also aiming for wide areas of organometallic chemistry including also complexes with a platinum-carbon-bond.

Ortho-metalation is one alternative for introducing a platinum-carbon-bond into platinum complexes. Although ortho-metalation of palladium and platinum amines is investigated since many years and ortho-metalation of palladium amines can proceed with high yields and with a large number of reactants, ortho-metalation of platinum amines (cycloplatination) remains a challenge. This is because platinum(II) is one of the most inert metal centers in coordination chemistry, resulting in low reaction rates and yields.

For example, the reaction of the standard starting compound potassium tetrachloroplatinate with N,N-dimethylbenzylamine can give at best a yield of 20% (Cope, A. C.; Friedrich, E. C.; *J. Am. Chem. Soc.;* 1968; 90; 909-913.).

Since the nineties research is focused on the reaction of cis-PtCl$_2$(dmso)$_2$ with amines. But even with this in other respects promising starting compound, only a cycloplatination of tertiary amines could initially be achieved (Ryabov, A. D.; Kazankov, G. M.; Panyashkina, I. M.; Grozovsky, O. V.; Dyachenko, O. G.; Polyakov, V. A.; Kuz'mina, L. G.; *J. Chem. Soc. Dalton Trans.;* 1997; 4385-4391.).

A recent publication (Capapé, A.; Crespo, M.; Granell, J.; Font-Bardia, M.; Solans, X.; *Dalton Trans.;* 2007; 2030-2039.) gives a yield of 10% for the reaction of benzylamine derivatives and underlines the difficulties in systematically synthesizing this class of compounds. The authors state in this publication: "It is interesting to point out that in spite of initial difficulties well established methods have now been developed for the cyclopalladation of primary amines, however, the preparation of platinum analogues still remains uncommon."

The object of the present invention is therefore to provide a process for preparing cycloplatinated platinum complexes on the basis of primary, secondary or tertiary amines, in particular on the basis of primary amines, which overcomes the described disadvantages, such as low yields, low reaction rates, restricted group of reactants, high excess of reactants and complex precursors, for example the synthesis of cis-PtCl$_2$(dmso)$_2$, and thereby making accessible a multitude of new compounds, which are of high interest in the field of pharmacy and catalysis.

An object of the present invention is a process for preparing trans-bisamine platinum(II) complexes and/or cycloplatinated platinum(II) complexes, wherein
  in a first process step, at least one halogenoplatinum(II) compound and/or pseudohalogenoplatinum(II) compound is reacted with hydroiodic acid and
  in a second process step, the product of the first process step is reacted with at least one primary or secondary or tertiary amine to form a trans-bisaminediiodoplatinum(II) complex and/or a cycloplatinated amineiodoplatinum(II) complex.

The process according to the invention has the advantage that, in particular due to the properties of the precursor prepared in the first process step, trans-bisaminediiodoplatinum(II) complexes and/or cycloplatinated amineiodoplatinum(II) complexes, in particular cycloplatinated amineiodoplatinum(II) complexes, may be prepared under mild reaction conditions, with short reaction times and/or with no or a small excess of reactants. A small amount of reactant is additionally advantageous, since it enables also the cost-effective use of expensive amines.

In the context of a preferred embodiment of the present invention, the product of the first process step is reacted in the second process step with at least one primary or secondary amine to form a trans-bisaminediiodoplatinum(II) complex and/or a cycloplatinated amineiodoplatinum(II) complex.

In the context of a particularly preferred embodiment of the present invention, the product of the first process step is reacted in the second process step with at least one primary amine to form a trans-bisaminediiodoplatinum(II) complex and/or a cycloplatinated amineiodoplatinum(II) complex.

In the context of the present invention, a "cycloplatinated platinum complex" is to be understood as a platinum complex, in which a platinum atom, a carbon atom bound to the platinum atom and a nitrogen atom bound to the platinum atom build up a ring, in particular a ring comprising a N—Pt—C-structure. A "cycloplatinated amineiodoplatinum (II) complex" is a special case thereof. In the context of the present invention, a "cycloplatinated amineiodoplatinum(II) complex" is to be understood as a complex of divalent platinum, which has a ring comprising a N—Pt—C-structure and additionally has an amine ligand, in particular a monodentate (monohapto-bound) amine ligand, bound to the platinum atom, and an iodo ligand bound to the platinum atom. The nitrogen/amine ligands bound to the platinum atom can thereby, for example be arranged trans with respect to each other.

In the context of the present invention, a tetrahalogenoplatinum(II) compound, for example a dihalogenoplatinum(II) compound and/or an alkali tetrahalogenoplatinum(II) compound and/or an ammonium tetrahalogenoplatinum(II) compound, in particular platinum dichloride, platinum dibromide, platinum diiodide, lithium tetrachloroplatinate, sodium tetrachloroplatinate, potassium tetrachloroplatinate, rubidium tetrachloroplatinate, cesium tetrachloroplatinate, ammonium tetrachloroplatinate, lithium tetrabromoplatinate, sodium tetrabromoplatinate, potassium tetrabromoplatinate, rubidium tetrabromoplatinate, cesium tetrabromoplatinate, ammonium tetrabromoplatinate, lithium tetraiodoplatinate, sodium tetraiodoplatinate, potassium tetraiodoplatinate, rubidium tetraiodoplatinate, cesium tetraiodoplatinate, ammonium tetraiodoplatinate, preferably lithium tetrachloroplatinate, sodium tetrachloroplatinate, potassium tetrachloroplatinate and/or ammonium tetrachloroplatinate is used as halogenoplatinum(II) compound; and/or platinum dicyanide and/or a tetracyanoplatinum(II) compound, for example an alkali tetracyanoplatinum(II) compound and/or an ammonium tetracyanoplatinum(II) compound, in particular lithium tetracyanoplatinate, sodium tetracyanoplatinate, potassium tetracyanoplatinate, rubidium tetracyanoplatinate, cesium tetracyanoplatinate and/or ammonium tetracyanoplatinate is used as pseudohalogenoplatinum(II) compound.

Preferably, in the context of the present invention, a primary or secondary or tertiary amine, in particular a primary amine, is used, which comprises at least one aromatic group, which has at least one hydrogen atom in ortho-position relative to the amine group being connected directly or indirectly to the aromatic group. In particular, a primary or secondary or tertiary amine, in particular a primary amine, can be used according to the invention, in which the amine group is connected via at least one carbon atom to an aromatic group, which has at least one hydrogen atom in ortho-position relative to the amine group being connected via one or more carbon atoms to the aromatic group. Preferably, in the context of the present invention, a primary or secondary or tertiary amine, in particular a primary amine is used, which comprises at least one chiral carbon atom and at least one aromatic group, whereas the aromatic group has at least one hydrogen atom in ortho-position relative to the amine group being directly or indirectly connected to the aromatic group. It is particularly preferred in the context of the present invention, to use a primary or secondary or tertiary amine, in particular a primary amine, in which the amine group is connected via at least one chiral carbon atom to an aromatic group, which has at least one hydrogen atom in ortho-position relative to the amine group being connected via one or more carbon atoms to the aromatic group.

In the context of a particularly preferred embodiment of the invention, the product of the first process step is reacted in the second process step with at least one primary or secondary or tertiary amine, in particular a chiral primary amine, to form a chiral trans-bisaminediiodoplatinum(II) complex and/or a chiral cycloplatinated amineiodoplatinum(II) complex. In the sense of the present invention, a compound, for example a primary, secondary or tertiary amine, a trans-bisaminediiodoplatinum(II) complex or rather a cycloplatinated amineiodoplatinum(II) complex, is named "chiral", if the compound has at least one chiral carbon atom.

In the context of the process according to the invention a primary or secondary or tertiary amine of the general formula:

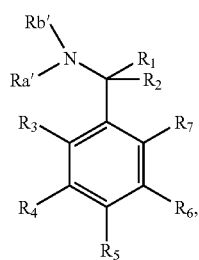

(i)

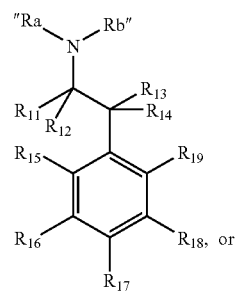

(ii)

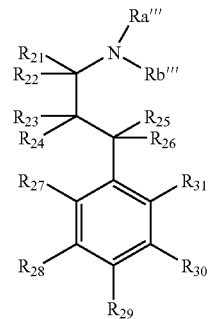

(iii)

can be used, whereas

Ra', Rb', Ra", Rb", Ra''', Rb''' each independently of one another represent hydrogen or a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a nitroso group or a silyl group having 1 to 10 carbon atoms, for example H, Me, Et, nPr, iPr, nBu, t-Bu, CMeEt, $C_6H_{11}$, $CF_3$, $C_2F_5$, Ph, $CH_2OH$, $CH_2OMe$, $CH_2OEt$, $CH_2OiPr$, $CH_2OnPr$, $CH_2OnBu$, $CH_2OtBu$, $CH_2OPh$, $C_2H_5OH$, $C_2H_5OMe$, $C_2H_5OEt$, $C_2H_5OnPr$, $C_2H_5OnPr$, $C_2H_5OnBu$, $C_2H_5OtBu$, $C_2H_5OPh$, OH, OMe, OEt, OnPr, OiPr, OnBu, OtBu, OPh, CHO, COMe, COEt, COnPr, COiPr, COnBu, COtBu, COPh, COCl, COBr, COI, COF, $COCF_3$, $COC_2F_5$, $COC_3F_7$, $CO_2H$, $CO_2Me$, $CO_2Et$, $CO_2nPr$, $CO_2iPr$, $CO_2nBu$, $CO_2tBu$, F, Cl, Br, I, $SO_2Me$, $SO_2Et$, $SO_2iPr$, $SO_2nPr$, $SO_2nBu$, $SO_2Bu$, $NH_2$, NO, $NHCH_2Ph$, $OSiMe_3$ or $OSiEt_3$, and/or $R_1$-$R_6$, $R_{11}$-$R_{18}$, $R_{21}$-$R_{30}$ each independently of one another represent hydrogen or a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a silyl group having 1 to 10 carbon atoms, for example H, Me, Et, nPr, iPr, nBu, t-Bu, CMeEt, $C_6H_{11}$, $CF_3$, $C_2F_5$, Ph, $CH_2OH$, $CH_2OMe$, $CH_2OEt$, $CH_2OiPr$, $CH_2OnPr$, $CH_2OnBu$, $CH_2OtBu$, $CH_2OPh$, $C_2H_5OH$, $C_2H_5OMe$, $C_2H_5OEt$, $C_2H_5OiPr$, $C_2H_5OnPr$, $C_2H_5OnBu$, $C_2H_5OtBu$, $C_2H_5OPh$, OH, OMe, OEt, OnPr, OiPr, OnBu, OtBu, OPh, CHO, COMe, COEt, COnPr, COiPr, COnBu, COtBu, COPh, COCl, COBr, COI, COF, $COCF_3$, $COC_2F_5$, $COC_3F_7$, $CO_2H$, $CO_2Me$, $CO_2Et$, $CO_2nPr$, $CO_2iPr$, $CO_2nBu$, $CO_2tBu$, F, Cl, Br, I, $SO_2Me$, $SO_2Et$, $SO_2iPr$, $SO_2nPr$, $SO_2nBu$, $SO_2Bu$, $NH_2$, $N(OH)_2$, NHMe, NHEt, NHnPr, NHiPr, NHnBu, NHtBu, $N(Me)_2$, $N(Et)_2$, NMeEt, $N(nPr)_2$, $N(nBu)_2$, $N(tBu)_2$, $OSiMe_3$ or $OSiEt_3$, and/or $R_1$ or $R_2$ and $R_3$, or $R_{13}$ or $R_{14}$ and $R_{15}$, or $R_{25}$ or $R_{26}$ and $R_{27}$ each represent an unsubstituted or substituted sp3 hybridized carbon atom, whereas $R_1$ or $R_2$ and $R_3$, or $R_{13}$ or $R_{14}$ and $R_{15}$, or $R_{25}$ or $R_{26}$ and $R_{27}$ are interconnected directly or via a further unsubstituted or substituted sp3 hybridized carbon atom in such a manner that a five-membered ring or six-membered ring is formed, and/or $R_{14}$ represents a π-electron and $R_{13}$ and $R_{15}$ each represent an unsubstituted or substituted sp2 hybridized carbon atom, whereas $R_{13}$ and $R_{15}$ are interconnected via a further unsubstituted or substituted sp2 hybridized carbon atom in such a manner that an aromatic six-membered ring is formed, or $R_{26}$ represents a π-electron and $R_{25}$ and $R_{27}$ each represent an unsubstituted or substituted sp2 hybridized carbon atom, whereas $R_{25}$ and $R_{27}$ are interconnected via a further unsubstituted or substituted sp2 hybridized carbon atom in such a manner that an aromatic six-membered ring is formed, and/or $R_{14}$ represents a π-electron and $R_{13}$ represents an unsubstituted or substituted sp2 hybridized carbon atom and $R_{15}$ represents an unsubstituted or substituted nitrogen atom, whereas $R_{13}$ and $R_{15}$ are interconnected in such a manner that an aromatic five-membered ring is formed, or $R_{26}$ represents a π-electron and $R_{25}$ represents an unsubstituted or substituted sp2 hybridized carbon atom and $R_{27}$ represents a nitrogen atom, whereas $R_{25}$ and $R_{27}$ are interconnected in such a manner that an aromatic five-membered ring is formed, and/or $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each represent an unsubstituted or substituted sp2 hybridized carbon atom, whereas $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each are interconnected via two further unsubstituted or substituted sp2 hybridized carbon atoms in such a manner that an aromatic six-membered ring or two aromatic six-membered rings are formed, and $R_7$, $R_{19}$, $R_{31}$ represent hydrogen.

In the context of the process according to the invention a primary amine of the general formula:

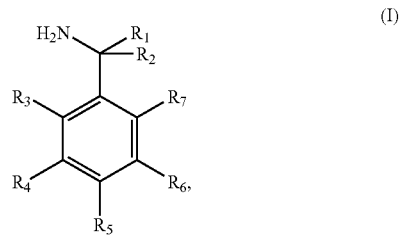

(I)

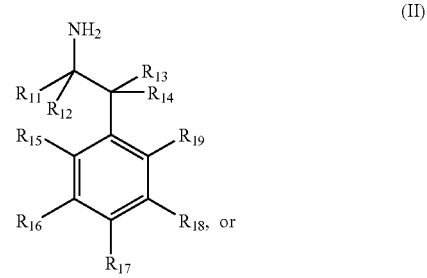

(II)

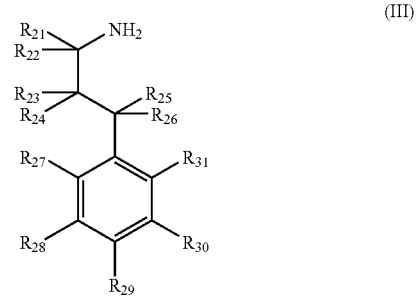

(III)

can in particular be used, whereas $R_1$-$R_6$, $R_{11}$-$R_{18}$, $R_{21}$-$R_{30}$ each independently of one another represent hydrogen or a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a silyl group having 1 to 10 carbon atoms, for example H, Me, Et, nPr, iPr, nBu, t-Bu, CMeEt, $C_6H_{11}$, $CF_3$, $C_2F_5$, Ph, $CH_2OH$, $CH_2OMe$, $CH_2OEt$, $CH_2OiPr$, $CH_2OnPr$, $CH_2OnBu$, $CH_2OtBu$, $CH_2OPh$, $C_2H_5OH$, $C_2H_5OMe$, $C_2H_5OEt$, $C_2H_5OiPr$, $C_2H_5OnPr$, $C_2H_5OnBu$, $C_2H_5OtBu$, $C_2H_5OPh$, OH, OMe, OEt, OnPr, OiPr, OnBu, OtBu, OPh, CHO, COMe, COEt, COnPr, COiPr, COnBu, COtBu, COPh, COCl, COBr, COI, COF, $COCF_3$, $COC_2F_5$, $COC_3F_7$, $CO_2H$, $CO_2Me$, CO$_2$Et, CO$_2$nPr, CO$_2$iPr, CO$_2$nBu, CO$_2$tBu, F, Cl, Br, I, SO$_2$Me, SO$_2$Et, SO$_2$iPr, SO$_2$nPr, SO$_2$nBu, SO$_2$Bu, NH$_2$, N(OH)$_2$, NHMe, NHEt, NHnPr, NHiPr, NHnBu, NHtBu, N(Me)$_2$, N(Et)$_2$, NMeEt, N(nPr)$_2$, N(nBu)$_2$, N(tBu)$_2$, OSiMe$_3$ or OSiEt$_3$, and/or R$_1$ or R$_2$ and R$_3$, or R$_{13}$ or R$_{14}$ and R$_{15}$, or R$_{25}$ or R$_{26}$ and R$_{27}$ each represent an unsubstituted or substituted sp3 hybridized carbon atom, whereas R$_1$ or R$_2$ and R$_3$, or R$_{13}$ or R$_{14}$ and R$_{15}$, or R$_{25}$ or R$_{26}$ and R$_{27}$ are interconnected directly or via a further unsubstituted or substituted sp3 hybridized carbon atom in such a manner that a five-membered ring or six-membered ring is formed, and/or R$_{14}$ represents a π-electron and R$_{13}$ and R$_{15}$ each represent an unsubstituted or substituted sp2 hybridized carbon atom, whereas R$_{13}$ and R$_{15}$ are interconnected via a further unsubstituted or substituted sp2 hybridized carbon atom in such a manner that an aromatic six-membered ring is formed, or R$_{26}$ represents a π-electron and R$_{25}$ and R$_{27}$ each represent an unsubstituted or substituted sp2 hybridized carbon atom, whereas R$_{25}$ and R$_{27}$ are interconnected via a further unsubstituted or substituted sp2 hybridized carbon atom in such a manner that an aromatic six-membered ring is formed, and/or R$_{14}$ represents a π-electron and R$_{13}$ represents an unsubstituted or substituted sp2 hybridized carbon atom and R$_{15}$ represents an unsubstituted or substituted nitrogen atom, whereas R$_{13}$ and R$_{15}$ are interconnected in such a manner that an aromatic five-membered ring is formed, or R$_{26}$ represents a π-electron and R$_{25}$ represents an unsubstituted or substituted sp2 hybridized carbon atom and R$_{27}$ represents a nitrogen atom, whereas R$_{25}$ and R$_{27}$ are interconnected in such a manner that an aromatic five-membered ring is formed, and/or R$_3$ and R$_4$ and/or R$_5$ and R$_6$ or R$_4$ and R$_5$, or R$_{15}$ and R$_{16}$ and/or R$_{17}$ and R$_{18}$ or R$_{16}$ and R$_{17}$, or R$_{27}$ and R$_{28}$ and/or R$_{29}$ and R$_{30}$ or R$_{28}$ and R$_{29}$ each represent an unsubstituted or substituted sp2 hybridized carbon atom, whereas R$_3$ and R$_4$ and/or R$_5$ and R$_6$ or R$_4$ and R$_5$, or R$_{15}$ and R$_{16}$ and/or R$_{17}$ and R$_{18}$ or R$_{16}$ and R$_{17}$, or R$_{27}$ and R$_{28}$ and/or R$_{29}$ and R$_{30}$ or R$_{28}$ and R$_{29}$ each are interconnected via two further unsubstituted or substituted sp2 hybridized carbon atoms in such a manner that an aromatic six-membered ring or two aromatic six-membered rings are formed, and R$_7$, R$_{19}$, R$_{31}$ represent hydrogen.

In the context of the present invention, "unsubstituted" means that the carbon atom or rather the nitrogen atom is bound to a hydrogen atom; "substituted" means that the carbon atom or rather the nitrogen atom is connected to an arbitrary moiety, in particular a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a silyl group having 1 to 10 carbon atoms, for example Me, Et, nPr, iPr, nBu, t-Bu, CMeEt, C$_6$H$_{11}$, CF$_3$, C$_2$F$_5$, Ph, CH$_2$OH, CH$_2$OMe, CH$_2$OEt, CH$_2$OiPr, CH$_2$OnPr, CH$_2$OnBu, CH$_2$OtBu, CH$_2$OPh, C$_2$H$_5$OH, C$_2$H$_5$OMe, C$_2$H$_5$OEt, C$_2$H$_5$OiPr, C$_2$H$_5$OnPr, C$_2$H$_5$OnBu, C$_2$H$_5$OtBu, C$_2$H$_5$OPh, OH, OMe, OEt, OnPr, OiPr, OnBu, OtBu, OPh, CHO, COMe, COEt, COnPr, COiPr, COnBu, COtBu, COPh, COCl, COBr, COI, COF, COCF$_3$, COC$_2$F$_5$, COC$_3$F$_7$, CO$_2$H, CO$_2$Me, CO$_2$Et, CO$_2$nPr, CO$_2$iPr, CO$_2$nBu, CO$_2$tBu, F, Cl, Br, I, SO$_2$Me, SO$_2$Et, SO$_2$iPr, SO$_2$nPr, SO$_2$nBu, SO$_2$Bu, NH$_2$, N(OH)$_2$, NHMe, NHEt, NHnPr, NHnPr, NHnBu, NHtBu, N(Me)$_2$, N(Et)$_2$, NMeEt, N(nPr)$_2$, N(nBu)$_2$, N(tBu)$_2$, OSiMe$_3$ or OSiEt$_3$.

As already explained, in the context of a preferred embodiment of the invention, a chiral primary or secondary or tertiary amine, in particular a chiral primary amine, is used. Preferably, the amines of the general formula (i), (ii), (iii), in particular the primary amines of the general formula (I), (II) and (III), have at least one chiral carbon atom. In the case of an amine of the general formula (i), (ii) or (iii), in particular in the case of a primary amine of the general formula (I), (II) or (III), this can for example be assured by R$_1$ being unlike R$_2$, or R$_{11}$ being unlike R$_{12}$ and/or R$_{13}$ being unlike R$_{14}$, or R$_{21}$ being unlike R$_{22}$ and/or R$_{23}$ being unlike R$_{24}$ and/or R$_{25}$ being unlike R$_{26}$.

Examples for primary amines suitable in the context of the present invention are: 2-fluorobenzylamine, 3-fluorobenzylamine, 4-fluorobenzylamine, 2-chlorobenzylamine, 3-chlorobenzylamine, 4-chlorobenzylamine, 2-bromobenzylamine, 3-bromobenzylamine, 4-bromobenzylamine, 2-iodobenzylamine, 3-iodobenzylamine, 4-iodobenzylamine, 2-methylbenzylamine, 3-methylbenzylamine, 4-methylbenzylamine, 2-ethylbenzylamine, 3-ethylbenzylamine, 4-ethylbenzylamine, 2-n-propylbenzylamine, 3-n-propylbenzylamine, 4-n-propylbenzylamine, 2-i-propylbenzylamine, 3-i-propylbenzylamine, 4-i-propylbenzylamine, 2-n-butylbenzylamine, 3-n-butylbenzylamine, 4-n-butylbenzylamine, 2-tert-butylbenzylamine, 3-tert-butylbenzylamine, 4-tert-butylbenzylamine, 2-hydroxybenzylamine, 3-hydroxybenzylamine, 4-hydroxybenzylamine, 2-methoxybenzylamine, 3-methoxybenzylamine, 4-methoxybenzylamine, 2-ethoxybenzylamine, 3-ethoxybenzylamine, 4-ethoxybenzylamine, 2-n-propoxybenzylamine, 3-n-propoxybenzylamine, 4-n-propoxybenzylamine, 2-i-propoxybenzylamine, 3-i-propoxybenzylamine, 4-i-propoxybenzylamine, 2-n-butoxybenzylamine, 3-n-butoxybenzylamine, 4-n-butoxybenzylamine, 2-tert-butoxybenzylamine, 3-tert-butoxybenzylamine, 4-tert-butoxybenzylamine, (R)-1-(2-fluorophenylethylamine), (S)-1-(2-fluorophenylethylamine), (R)-1-(2-chlorophenylethylamine), (S)-1-(2-chlorophenylethylamine), (R)-1-(2-bromophenylethylamine), (S)-1-(2-bromophenylethylamine), (R)-1-(2-iodophenylethylamine), (S)-1-(2-iodophenylethylamine), (R)-1-(2-methylphenylethylamine), (S)-1-(2-methylphenylethylamine), (R)-1-(2-ethylphenylethylamine), (S)-1-(2-ethylphenylethylamine), (R)-1-(2-n-propylphenylethylamine), (S)-1-(2-n-propylphenylethylamine), (R)-1-(2-i-propylphenylethylamine), (S)-1-(2-i-propylphenylethylamine), (R)-1-(2-n-butylphenylethylamine), (S)-1-(2-n-butylphenylethylamine), (R)-1-(2-tert-butylphenylethylamine), (S)-1-(2-tert-butylphenylethylamine), (R)-1-(2-hydroxyphenylethylamine), (S)-1-(2-hydroxyphenylethylamine), (R)-1-(2-methoxyphenylethylamine), (S)-1-(2-methoxyphenylethylamine), (R)-1-(2-ethoxyphenylethylamine), (S)-1-(2-ethoxyphenylethylamine), (R)-1-(2-n-propoxyphenylethylamine), (S)-1-(2-n-propoxyphenylethylamine), (R)-1-(2-i- propoxyphenylethylamine), (S)-1-(2-i-propoxyphenylethylamine), (R)-1-(2-n-butoxyphenylethylamine), (S)-1-(2-n-butoxyphenylethylamine), (R)-1-(2-tert-butoxyphenylethylamine), (S)-1-(2-tert-butoxyphenylethylamine), (R)-1-(3-fluorophenylethylamine), (S)-1-(3-fluorophenylethylamine), (R)-1-(3-chlorophenylethylamine), (S)-1-(3-chlorophenylethylamine), (R)-1-(3-bromophenylethylamine), (S)-1-(3-bromophenylethylamine), (R)-1-(3-iodophenylethylamine), (S)-1-(3-iodophenylethylamine), (R)-1-(3-methylphenylethylamine), (S)-1-(3-methylphenylethylamine), (R)-1-(3-ethylphenylethylamine), (S)-1-(3-ethylphenylethylamine), (R)-1-(3-n-propylphenylethylamine), (S)-1-(3-n-propylphenylethylamine), (R)-1-(3-i-propylphenylethylamine), (S)-1-(3-i-propylphenylethylamine), (R)-1-(3-n-butylphenylethylamine), (S)-1-(3-n-butylphenylethylamine), (R)-1-(3-tert-butylphenylethylamine), (S)-1-(3-tert-butylphenylethylamine), (R)-1-(3-hydroxyphenylethylamine), (S)-1-(3-hydroxyphenylethylamine), (R)-1-(3-methoxyphenylethylamine), (S)-1-(3-methoxyphenylethylamine), (R)-1-(3-ethoxyphenylethylamine), (S)-1-(3-ethoxyphenylethylamine), (R)-1-(3-n-propoxyphenylethylamine), (S)-1-(3-n-propoxyphenylethylamine), (R)-1-(3-i-propoxyphenylethylamine), (S)-1-(3-i-propoxyphenylethylamine), (R)-1-(3-n-butoxyphenylethylamine), (S)-1-(3-n-butoxyphenylethylamine), (R)-1-(3-tert-butoxyphenylethylamine), (S)-1-(3-tert-butoxyphenylethylamine), (R)-1-(4-fluorophenylethylamine), (S)-1-(4-fluorophenylethylamine), (R)-1-(4-chlorophenylethylamine), (S)-1-(4-chlorophenylethylamine), (R)-1-(4-bromophenylethylamine), (S)-1-(4-bromophenylethylamine), (R)-1-(4-iodophenylethylamine), (S)-1-(4-iodophenylethylamine), (R)-1-(4-methylphenylethylamine), (S)-1-(4-methylphenylethylamine), (R)-1-(4-ethylphenylethylamine), (S)-1-(4-ethylphenylethylamine), (R)-1-(4-n-propylphenylethylamine), (S)-1-(4-n-propylphenylethylamine), (R)-1-(4-i-propylphenylethylamine), (S)-1-(4-i-propylphenylethylamine), (R)-1-(4-n-butylphenylethylamine), (S)-1-(4-n-butylphenylethylamine), (R)-1-(4-tert-butylphenylethylamine), (S)-1-(4-tert-butylphenylethylamine), (R)-1-(4-hydroxyphenylethylamine), (S)-1-(4-hydroxyphenylethylamine), (R)-1-(4-methoxyphenylethylamine), (S)-1-(4-methoxyphenylethylamine), (R)-1-(4-ethoxyphenylethylamine), (S)-1-(4-ethoxyphenylethylamine), (R)-1-(4-n-propoxyphenylethylamine), (S)-1-(4-n-propoxyphenylethylamine), (R)-1-(4-i-propoxyphenylethylamine), (S)-1-(4-i-propoxyphenylethylamine), (R)-1-(4-n-butoxyphenylethylamine), (S)-1-(4-n-butoxyphenylethylamine), (R)-1-(4-tert-butoxyphenylethylamine), (S)-1-(4-tert-butoxyphenylethylamine), 2-Phenylethylamine, dopamine, noradrenaline, D-phenylalaninemethylester, L-phenylalaninemethylester, L-DOPA, tryptamine, DL-tryptophan, D-tryptophan, L-tryptophan, 1-(1-naphthyl)-ethylamine, 1-aminotetralin, 1-aminoindan and amphetamine.

Examples for secondary amines suitable in the context of the present invention are: N-methyl derivatives of phenylethylamines, for example (R)—N-methyl-1-(2-fluorophenylethylamine), (S)—N-methyl-1-(2-fluorophenylethylamine), (R)—N-methyl-1-(2-chlorophenylethylamine), (S)—N-methyl-1-(2-chlorophenylethylamine), (R)—N-methyl-1-(2-bromophenylethylamine), (S)—N-methyl-1-(2-bromophenylethylamine), (R)—N-methyl-1-(2-iodophenylethylamine), (S)—N-methyl-1-(2-iodophenylethylamine), (R)—N-methyl-1-(2-methylphenylethylamine), (S)—N-methyl-1-(2-methylphenylethylamine), (R)—N-methyl-1-(2-ethylphenylethylamine), (S)—N-methyl-1-(2-ethylphenylethylamine), (R)—N-methyl-1-(2-n-propylphenylethylamine), (S)—N-methyl-1-(2-n-propylphenylethylamine), (R)—N-methyl-1-(2-i-propylphenylethylamine), (S)—N-methyl-1-(2-i-propylphenylethylamine), (R)—N-methyl-1-(2-n-butylphenylethylamine), (S)—N-methyl-1-(2-n-butylphenylethylamine), (R)—N-methyl-1-(2-tert-butylphenylethylamine), (S)—N-methyl-1-(2-tert-butylphenylethylamine), (R)—N-methyl-1-(2-hydroxyphenylethylamine), (S)—N-methyl-1-(2-hydroxyphenylethylamine), (R)—N-methyl-1-(2-methoxyphenylethylamine), (S)—N-methyl-1-(2-methoxyphenylethylamine), (R)—N-methyl-1-(2-ethoxyphenylethylamine), (S)—N-methyl-1-(2-ethoxyphenylethylamine), (R)—N-methyl-1-(2-n-propoxyphenylethylamine), (S)—N-methyl-1-(2-n-propoxyphenylethylamine), (R)—N-methyl-1-(2-i-propoxyphenylethylamine), (S)—N-methyl-1-(2-i-propoxyphenylethylamine), (R)—N-methyl-1-(2-n-butoxyphenylethylamine), (S)—N-methyl-1-(2-n-butoxyphenylethylamine), (R)—N-methyl-1-(2-tert-butoxyphenylethylamine), (S)—N-methyl-1-(2-tert-butoxyphenylethylamine), (R)—N-methyl-1-(3-fluorophenylethylamine), (S)—N-methyl-1-(3-fluorophenylethylamine), (R)—N-methyl-1-(3-chlorophenylethylamine), (S)—N-methyl-1-(3-chlorophenylethylamine), (R)—N-methyl-1-(3-bromophenylethylamine), (S)—N-methyl-1-(3-bromophenylethylamine), (R)—N-methyl-1-(3-iodophenylethylamine), (S)—N-methyl-1-(3-iodophenylethylamine), (R)—N-methyl-1-(3-methylphenylethylamine), (S)—N-methyl-1-(3-methylphenylethylamine), (R)—N-methyl-1-(3-ethylphenylethylamine), (S)—N-methyl-1-(3-ethylphenylethylamine), (R)—N-methyl-1-(3-n-propylphenylethylamine), (S)—N-methyl-1-(3-n-propylphenylethylamine), (R)—N-methyl-1-(3-i-propylphenylethylamine), (S)—N-methyl-1-(3-i-propylphenylethylamine), (R)—N-methyl-1-(3-n-butylphenylethylamine), (S)—N-methyl-1-(3-n-butylphenylethylamine), (R)—N-methyl-1-(3-tert-butylphenylethylamine), (S)—N-methyl-1-(3-tert-butylphenylethylamine), (R)—N-methyl-1-(3-hydroxyphenylethylamine), (S)—N-methyl-1-(3-hydroxyphenylethylamine), (R)—N-methyl-1-(3-methoxyphenylethylamine), (S)—N-methyl-1-(3-methoxyphenylethylamine), (R)—N-methyl-1-(3-ethoxyphenylethylamine), (S)—N-methyl-1-(3-ethoxyphenylethylamine), (R)—N-methyl-1-(3-n-propoxyphenylethylamine), (S)—N-methyl-1-(3-n-propoxyphenylethylamine), (R)—N-methyl-1-(3-i-propoxyphenylethylamine), (S)—N-methyl-1-(3-i-propoxyphenylethylamine), (R)—N-methyl-1-(3-n-butoxyphenylethylamine), (S)—N-methyl-1-(3-n-butoxyphenylethylamine), (R)—N-methyl-1-(3-tert-butoxyphenylethylamine), (S)—N-methyl-1-(3-tert-butoxyphenylethylamine), (R)—N-methyl-1-(4-fluorophenylethylamine), (S)—N-methyl-1-(4-fluorophenylethylamine), (R)—N-methyl-1-(4-chlorophenylethylamine), (S)—N-methyl-1-(4-chlorophenylethylamine), (R)—N-methyl-1-(4-bromophenylethylamine), (S)—N-methyl-1-(4-bromophenylethylamine), (R)—N-methyl-1-(4- iodophenylethylamine), (S)—N-methyl-1-(4-iodophenyl-ethylamine), (R)—N-methyl-1-(4-methylphenylethylamine), (S)—N-methyl-1-(4-methylphenylethylamine), (R)—N-methyl-1-(4-ethylphenylethylamine), (S)—N-methyl-1-(4-ethylphenylethylamine), (R)—N-methyl-1-(4-n-propylphenylethylamine), (S)—N-methyl-1-(4-n-propylphenylethylamine), (R)—N-methyl-1-(4-i-propylphenylethylamine), (S)—N-methyl-1-(4-i-propylphenylethylamine), (R)—N-methyl-1-(4-n-butylphenylethylamine), (S)—N-methyl-1-(4-n-butylphenylethylamine), (R)—N-methyl-1-(4-tert-butylphenylethylamine), (S)—N-methyl-1-(4-tert-butylphenylethylamine), (R)—N-methyl-1-(4-hydroxyphenylethylamine), (S)—N-methyl-1-(4-hydroxyphenylethylamine), (R)—N-methyl-1-(4-methoxyphenylethylamine), (S)—N-methyl-1-(4-methoxyphenylethylamine), (R)—N-methyl-1-(4-ethoxyphenylethylamine), (S)—N-methyl-1-(4-ethoxyphenylethylamine), (R)—N-methyl-1-(4-n-propoxyphenylethylamine), (S)—N-methyl-1-(4-n-propoxyphenylethylamine), (R)—N-methyl-1-(4-i-propoxyphenylethylamine), (S)—N-methyl-1-(4-i-propoxyphenylethylamine), (R)—N-methyl-1-(4-n-butoxyphenylethylamine), (S)—N-methyl-1-(4-n-butoxyphenylethylamine), (R)—N-methyl-1-(4-tert-butoxyphenylethylamine) and/or (S)—N-methyl-1-(4-tert-butoxyphenylethylamine).

Examples for tertiary amines suitable in the context of the present invention are: N,N-dimethyl derivatives, for example (R)—N,N-dimethyl-1-(2-fluorophenylethylamine), (S)—N,N-dimethyl-1-(2-fluorophenylethylamine), (R)—N,N-dimethyl-1-(2-chlorophenylethylamine), (S)—N,N-dimethyl-1-(2-chlorophenylethylamine), (R)—N,N-dimethyl-1-(2-bromophenylethylamine), (S)—N,N-dimethyl-1-(2-bromophenylethylamine), (R)—N,N-dimethyl-1-(2-iodophenylethylamine), (S)—N,N-dimethyl-1-(2-iodophenylethylamine), (R)—N,N-dimethyl-1-(2-methylphenylethylamine), (S)—N,N-dimethyl-1-(2-methylphenylethylamine), (R)—N,N-dimethyl-1-(2-ethylphenylethylamine), (S)—N,N-dimethyl-1-(2-ethylphenylethylamine), (R)—N,N-dimethyl-1-(2-n-propylphenylethylamine), (S)—N,N-dimethyl-1-(2-n-propylphenylethylamine), (R)—N,N-dimethyl-1-(2-i-propylphenylethylamine), (S)—N,N-dimethyl-1-(2-i-propylphenylethylamine), (R)—N,N-dimethyl-1-(2-n-butylphenylethylamine), (S)—N,N-dimethyl-1-(2-n-butylphenylethylamine), (R)—N,N-dimethyl-1-(2-tert-butylphenylethylamine), (S)—N,N-dimethyl-1-(2-tert-butylphenylethylamine), (R)—N,N-dimethyl-1-(2-hydroxyphenylethylamine), (S)—N,N-dimethyl-1-(2-hydroxyphenylethylamine), (R)—N,N-dimethyl-1-(2-methoxyphenylethylamine), (S)—N,N-dimethyl-1-(2-methoxyphenylethylamine), (R)—N,N-dimethyl-1-(2-ethoxyphenylethylamine), (S)—N,N-dimethyl-1-(2-ethoxyphenylethylamine), (R)—N,N-dimethyl-1-(2-n-propoxyphenylethylamine), (S)—N,N-dimethyl-1-(2-n-propoxyphenylethylamine), (R)—N,N-dimethyl-1-(2-i-propoxyphenylethylamine), (S)—N,N-dimethyl-1-(2-i-propoxyphenylethylamine), (R)—N,N-dimethyl-1-(2-n-butoxyphenylethylamine), (S)—N,N-dimethyl-1-(2-n-butoxyphenylethylamine), (R)—N,N-dimethyl-1-(2-tert-butoxyphenylethylamine), (S)—N,N-dimethyl-1-(2-tert-butoxyphenylethylamine), (R)—N,N-dimethyl-1-(3-fluorophenylethylamine), (S)—N,N-dimethyl-1-(3-fluorophenylethylamine), (R)—N,N-dimethyl-1-(3-chlorophenylethylamine), (S)—N,N-dimethyl-1-(3-chlorophenylethylamine), (R)—N,N-dimethyl-1-(3-bromophenylethylamine), (S)—N,N-dimethyl-1-(3-bromophenylethylamine), (R)—N,N-dimethyl-1-(3-iodophenylethylamine), (S)—N,N-dimethyl-1-(3-iodophenylethylamine), (R)—N,N-dimethyl-1-(3-methylphenylethylamine), (S)—N,N-dimethyl-1-(3-methylphenylethylamine), (R)—N,N-dimethyl-1-(3-ethylphenylethylamine), (S)—N,N-dimethyl-1-(3-ethylphenylethylamine), (R)—N,N-dimethyl-1-(3-n-propylphenylethylamine), (S)—N,N-dimethyl-1-(3-n-propylphenylethylamine), (R)—N,N-dimethyl-1-(3-i-propylphenylethylamine), (S)—N,N-dimethyl-1-(3-i-propylphenylethylamine), (R)—N,N-dimethyl-1-(3-n-butylphenylethylamine), (S)—N,N-dimethyl-1-(3-n-butylphenylethylamine), (R)—N,N-dimethyl-1-(3-tert-butylphenylethylamine), (S)—N,N-dimethyl-1-(3-tert-butylphenylethylamine), (R)—N,N-dimethyl-1-(3-hydroxyphenylethylamine), (S)—N,N-dimethyl-1-(3-hydroxyphenylethylamine), (R)—N,N-dimethyl-1-(3-methoxyphenylethylamine), (S)—N,N-dimethyl-1-(3-methoxyphenylethylamine), (R)—N,N-dimethyl-1-(3-ethoxyphenylethylamine), (S)—N,N-dimethyl-1-(3-ethoxyphenylethylamine), (R)—N,N-dimethyl-1-(3-n-propoxyphenylethylamine), (S)—N,N-dimethyl-1-(3-n-propoxyphenylethylamine), (R)—N,N-dimethyl-1-(3-i-propoxyphenylethylamine), (S)—N,N-dimethyl-1-(3-i-propoxyphenylethylamine), (R)—N,N-dimethyl-1-(3-n-butoxyphenylethylamine), (S)—N,N-dimethyl-1-(3-n-butoxyphenylethylamine), (R)—N,N-dimethyl-1-(3-tert-butoxyphenylethylamine), (S)—N,N-dimethyl-1-(3-tert-butoxyphenylethylamine), (R)—N,N-dimethyl-1-(4-fluorophenylethylamine), (S)—N,N-dimethyl-1-(4-fluorophenylethylamine), (R)—N,N-dimethyl-1-(4-chlorophenylethylamine), (S)—N,N-dimethyl-1-(4-chlorophenylethylamine), (R)—N,N-dimethyl-1-(4-bromophenylethylamine), (S)—N,N-dimethyl-1-(4-bromophenylethylamine), (R)—N,N-dimethyl-1-(4-iodophenylethylamine), (S)—N,N-dimethyl-1-(4-iodophenylethylamine), (R)—N,N-dimethyl-1-(4-methylphenylethylamine), (S)—N,N-dimethyl-1-(4-methylphenylethylamine), (R)—N,N-dimethyl-1-(4-ethylphenylethylamine), (S)—N,N-dimethyl-1-(4-ethylphenylethylamine), (R)—N,N-dimethyl-1-(4-n-propylphenylethylamine), (S)—N,N-dimethyl-1-(4-n-propylphenylethylamine), (R)—N,N-dimethyl-1-(4-i-propylphenylethylamine), (S)—N,N-dimethyl-1-(4-i-propylphenylethylamine), (R)—N,N-dimethyl-1-(4-n-butylphenylethylamine), (S)—N,N-dimethyl-1-(4-n-butylphenylethylamine), (R)—N,N-dimethyl-1-(4-tert-butylphenylethylamine), (S)—N,N-dimethyl-1-(4-tert-butylphenylethylamine), (R)—N,N-dimethyl-1-(4-hydroxyphenylethylamine), (S)—N,N-dimethyl-1-(4-hydroxyphenylethylamine), (R)—N,N-dimethyl-1-(4-methoxyphenylethylamine), (S)—N,N-dimethyl-1-(4-methoxyphenylethylamine), (R)—N,N-dimethyl-1-(4-ethoxyphenylethylamine), (S)—N,N-dimethyl-1-(4-ethoxyphenylethylamine), (R)—N,N-dimethyl-1-(4-n-propoxyphenylethylamine), (S)—N,N-dimethyl-1-(4-n-propoxyphenylethylamine), (R)—N,N-dimethyl-1-(4-i-propoxyphenylethylamine), (S)—N,N-dimethyl-1-(4-i-propoxyphenylethylamine), (R)—N,N-dimethyl-1-(4-n-butoxyphenylethylamine), (S)—N,N-dimethyl-1-(4-n-butoxyphenylethylamine), (R)—N,N-dimethyl-1-(4-tert-butoxyphenylethylamine), (S)—N,N-dimethyl-1-(4-tert-butoxyphenylethylamine).

In the context of an embodiment of the process according to the invention, in a first process step, at least one halogenoplatinum(II) compound and/or pseudohalogenoplatinum(II) compound is dissolved in water, hydroiodic acid is added to the solution and the water is subsequently removed, whereas a solid is obtained; and in a second process step, the solid of the first process step is suspended/solved in at least one alcohol and/or water and reacted with a primary, secondary or tertiary amine, in particular a primary amine, to form a trans-bisaminediiodoplatinum(II) complex and/or a cycloplatinated amineiodoplatinum(II) complex.

However, in the context of the present invention, it is also possible to omit the steps of removing water and subsequent re-dispersing/dissolving. In this case, it turned out to be convenient to control the pH value, for example by adding a sodium hydroxide solution.

Hydroiodic acid can be used in the context of the present invention as aqueous hydroiodic acid solution having a concentration of $\geq 45$ percent by weight, for example of $\geq 55$ percent by weight or $\geq 67$ percent by weight, referring to the overall weight of the solution. In the context of an embodiment of the process according to the invention, the aqueous hydroiodic acid solution has a concentration of $\geq 55$ percent by weight to $\leq 60$ percent by weight, for example of 57 percent by weight, referring to the overall weight of the solution.

Preferably, hydroiodic acid is added in excess. The stoichiometric ratio of halogenoplatinum(II) compound and/or pseudohalogenoplatinum(II) compound to hydroiodic acid can be within a range of $\geq 1:2$ to $\leq 1:6$, for example of $\geq 1:3$ to $\leq 1:5$, in particular of $\geq 1:3,5$ to $\leq 1:4,5$. For example the ratio of halogenoplatinum(II) compound and/or pseudohalogenoplatinum(II) compound to hydroiodic acid can be 1:4.

It is useful to stir the reaction mixture for $\geq 3$ min to $\leq 4$ h, for example for $\geq 5$ min to $\leq 2$ h, after adding hydroiodic acid. Stirring can thereby carried out at room temperature.

In the context of the present invention, it advantageously turned out that for carrying out the process according to the invention a molar ratio of primary, secondary or tertiary amine, in particular primary amine, to the product of the first process step of 3:1 can be sufficient. However, for enhancing the reaction rate and yield, it can eventually be advantageous to provide a slight to high amine excess. In the context of an embodiment of the invention the molar ratio of primary, secondary or tertiary amine, in particular primary amine, to product of the first process step is, for example within a range of $\geq 3:1$ to $\leq 5:1$.

In the second process step, the at least one alcohol can for example be selected from the group comprising methanol, ethanol and/or isopropanol. Preferably, in the second process step, an alcohol-water mixture, for example a mixture of methanol and/or ethanol and water, in particular a methanol-water mixture, is used. The volume ratio of alcohol to water can for example be within a range of $\geq 1:1$ to $\leq 5:1$, in particular of $\geq 1.5:1$ to $\leq 3:1$.

Preferably, the reaction mixture is heated to reflux in the second process step. The reaction mixture can be heated to reflux in the second process step for $\geq 5$ min, for example $\geq 10$ min to $\leq 16$ h, preferably for $\geq 15$ min to $\leq 10$ h, particularly preferred for $\geq 20$ min to $\leq 5$ h.

In the context of the present invention, it turned out that during the process according to the invention initially a trans-bisaminediiodoplatinum(II) complex is formed, which by and by continues to react to form a cycloplatinated amineiodoplatinum(II) complex. Therefore, by a short reaction time the trans-bisaminediiodoplatinum(II) complex and by a long reaction time the cycloplatinated amineiodoplatinum(II) complex can be synthesized. The "shortness" or rather "length" of the reaction time thereby depends on the used primary amine. As shown by the examples, the reaction time for synthesizing trans-bisaminediiodoplatinum(II) complexes is about one eighth of the reaction time for the complete conversion to the corresponding cycloplatinated amineiodoplatinum complex. It turned out that the trans-bisaminediiodoplatinum(II) complex can be isolated by concentrating the solvent and/or by adding an appropriate solvent, for example water.

In the context of a further embodiment of the process according to the invention, the trans-bisaminediiodoplatinum(II) complex and/or the cycloplatinated amineiodoplatinum(II) complex, in particular the cycloplatinated amineiodoplatinum(II) complex, of the second process step, is subjected in a third process step to a ligand exchange reaction, in which at least one amine ligand, in particular monodentate amine ligand, and/or at least one iodo ligand is replaced by another ligand.

For example, in the third process step according to the invention, at least one amine ligand, in particular monodentate amine ligand, and/or at least one iodo ligand is replaced by a halogen atom, for example I, Cl, Br, F, or a pseudohalogen, for example NC, SCN, NCS, OCN, NCO, $N_3$, NCSe, or a $C_6F_5$ ligand or an unsubstituted or substituted, linear or branched alkylamine or an unsubstituted or substituted, linear or branched alkenylamine or an unsubstituted or substituted alkynylamine or an unsubstituted or substituted, linear or branched arylalkylamine, for example an amine of the general formula (i), (ii), (iii), in particular a primary amine of the general formula (I), (II) or (III), or a phosphane, for example $P(Ph)_3$, $P(C_6H_{11})_3$, $P(Me)_3$, $P(Et)_3$, $P(nPr)_3$, $P(iPr)_3$, $P(nBu)_3$, $P(tBu)_3$, $PCl_3$, $PF_3$, $PI_3$, $PBr_3$, or a N-heterocycle, for example pyridine, or a S-heterocycle, for example thiophene, and/or an amine ligand, in particular a monodentate amine ligand, and an iodo ligand are replaced by a chelate ligand, for example a bis(dialkylphosphino)alkane, bis(diphenylphosphino)alkane, bis(dialkylphosphino)alkene, bis(diphenylphosphino)alkene, an alkylene diamine, an oxalate, 2,2'-bis(diphenylphosphino)-1,1'-binaphthyl (BINAP), ethanolamine(2-aminoethanol), thioethanolamine(2-aminoethanethiol), 1,1'-bis(diphenyl)phosphinoferrocene, 2-piperidylmethanol, glycerine, glycolic acid, 1,2-diaminocyclohexane, malonic acid, tetramethylethylenediamine, ethylenediaminetetraacetic acid, N,N'-ribavirin(1-beta-D-ribofuranosyl-1,2,4-triazol-3-carboxamide), acetylacetonate or 2,2'-bipyridine. In particular both iodo ligand and/or both amine ligands, in particular monodentate amine ligands, of the trans-bisaminediiodoplatinum(II) complex can each identically or independently of one another be replaced by a halogen atom, for example Cl, Br, F, or a pseudohalogen, for example NC, SCN, NCS, OCN, NCO, $N_3$, NCSe, or a $C_6F_5$ ligand or an unsubstituted or substituted, linear or branched alkylamine or an unsubstituted or substituted, linear or branched alkenylamine or an unsubstituted or substituted alkynylamine or an unsubstituted or substituted, linear or branched arylalkylamine, for example an amine of the general formula (i), (ii), (iii), in particular a primary amine of the general formula (I), (II) or (III), or a phosphane, for example $P(Ph)_3$, $P(C_6H_{11})_3$, $P(Me)_3$, $P(Et)_3$, $P(nPr)_3$, $P(iPr)_3$, $P(nBu)_3$, $P(tBu)_3$, $PCl_3$, $PF_3$, $PI_3$, $PBr_3$, or a N-heterocycle, for example pyridine, or a S-heterocycle, for example thiophene. Preferably, in the context of the present invention, the amine ligand, in particular the monodentate amine ligand, of the cycloplatinated amineiodoplatinum(II) complex is replaced by a halogen atom, for example I, Cl, Br, F, or a pseudohalogen, for example NC, SCN, NCS, OCN, NCO, $N_3$, NCSe, or a $C_6F_5$ ligand or an unsubstituted or substituted, linear or branched alkylamine or an unsubstituted or substituted, linear or branched alkenylamine or an unsubstituted or substituted alkynylamine or an unsubstituted or substituted, linear or branched arylalkylamine, for example an amine of the general formula (i), (ii), (iii), in particular a primary amine of the general formula (I), (II) or (III), a phosphane, for example P(Ph)$_3$, P(C$_6$H$_{11}$)$_3$, P(Me)$_3$, P(Et)$_3$, P(nPr)$_3$, P(iPr)$_3$, P(nBu)$_3$, P(tBu)$_3$, PCl$_3$, PF$_3$, PI$_3$, PBr$_3$, or a N-heterocycle, for example pyridine, or a S-heterocycle, for example thiophene; and/or the iodo ligand of the cycloplatinated amineiodoplatinum(II) complexes is replaced by a halogen atom, for example Cl, Br, F, or a pseudohalogen, for example NC, SCN, NCS, OCN, NCO, N$_3$, NCSe, or a C$_6$F$_5$ ligand or an unsubstituted or substituted, linear or branched alkylamine or an unsubstituted or substituted, linear or branched alkenylamine or an unsubstituted or substituted alkynylamine or an unsubstituted or substituted, linear or branched arylalkylamine, for example an amine of the general formula (i), (ii), (iii), in particular a primary amine of the general formula (I), (II) or (III), or a phosphane, for example P(Ph)$_3$, P(C$_6$H$_{11}$)$_3$, P(Me)$_3$, P(Et)$_3$, P(nPr)$_3$, P(iPr)$_3$, P(nBu)$_3$, P(tBu)$_3$, PCl$_3$, PF$_3$, PI$_3$, PBr$_3$, or a N-heterocycle, for example pyridine, or a S-heterocycle, for example thiophene, or the amine ligand, in particular the monodentate amine ligand, and the iodo ligand of the cycloplatinated amineiodoplatinum(II) complex is replaced by a chelate ligand, for example a bis(dialkylphosphino)alkane, bis(diphenylphosphino)alkane, bis(dialkylphosphino)alkene, bis(diphenylphosphino)alkene, an alkylene diamine, an oxalate, 2,2'-bis(diphenylphosphino)-1,1'-binaphthyl (BINAP), ethanolamine(2-amineoethanol), thioethanolamine(2-aminoethanethiol), 1,1'-bis(diphenyl)phosphinoferrocene, 2-piperidylmethanol, glycerine, glycolic acid, 1,2-diaminocyclohexane, malonic acid, tetramethylethylenediamine, ethylenediaminetetraacetic acid, N,N'-ribavirin(1-beta-D-ribofuranosyl-1,2,4-triazol-3-carboxamide), acetylacetonate or 2,2'-bipyridine. For example, the cycloplatinated amineiodoplatinum(II) complex can be subjected in the third process step to a ligand exchange reaction, in which the complex is reacted with silver acetylacetonate or a silver salt of a weakly coordinating anion in the presence of a chelating ligand, such as 2,2'-bipyridine.

A further object of the present invention relates to chiral trans-bisaminediiodoplatinum(II) complexes and chiral cycloplatinated amineiodoplatinum(II) complexes obtainable by the process according to the invention.

A further object of the present invention relates cycloplatinated amineiodoplatinum(II) complexes of the general formula:

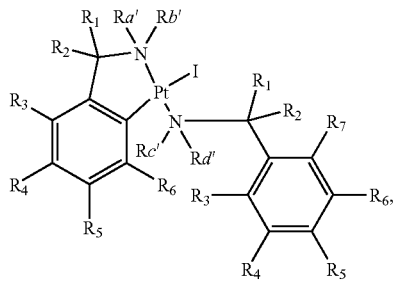

(iv)

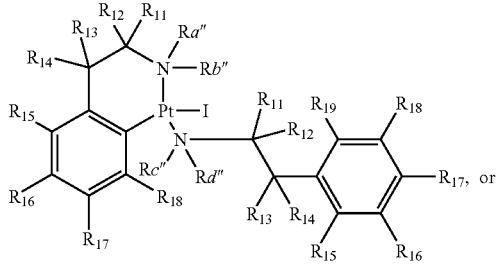

(v)

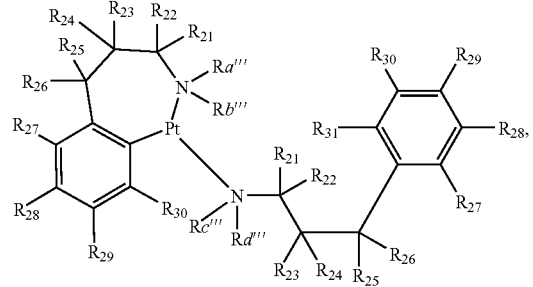

(vi)

whereas:

Ra'-Rd', Ra''-Rd'', Ra'''-Rd''' each independently of one another represent hydrogen or a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a nitroso group or a silyl group having 1 to 10 carbon atoms, for example H, Me, Et, nPr, iPr, nBu, t-Bu, CMeEt, C$_6$H$_{11}$, CF$_3$, C$_2$F$_5$, Ph, CH$_2$OH, CH$_2$OMe, CH$_2$OEt, CH$_2$OiPr, CH$_2$OnPr, CH$_2$OnBu, CH$_2$OtBu, CH$_2$OPh, C$_2$H$_5$OH, C$_2$H$_5$OMe, C$_2$H$_5$OEt, C$_2$H$_5$OiPr, C$_2$H$_5$OnPr, C$_2$H$_5$OnBu, C$_2$H$_5$OtBu, CH$_2$OPh, OH, OMe, OEt, OnPr, OiPr, OnBu, OtBu, OPh, CHO, COMe, COEt, COnPr, COiPr, COnBu, COtBu, COPh, COCl, COBr, COI, COF, COCF$_3$, COC$_2$F$_5$, COC$_3$F$_7$, CO$_2$H, CO$_2$Me, CO$_2$Et, CO$_2$nPr, CO$_2$iPr, CO$_2$nBu, CO$_2$tBu, F, Cl, Br, I, SO$_2$Me, SO$_2$Et, SO$_2$iPr, SO$_2$nPr, SO$_2$nBu, SO$_2$Bu, NH$_2$, NO, NHCH$_2$Ph, OSiMe$_3$ or OSiEt$_3$, and/or R$_1$-R$_6$, R$_{11}$-R$_{18}$, R$_{21}$-R$_{30}$ each independently of one another represent hydrogen or a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a silyl group having 1 to 10 carbon atoms, for example H, Me, Et, nPr, iPr, nBu, t-Bu, CMeEt, $C_6H_{11}$, $CF_3$, $C_2F_5$, Ph, $CH_2OH$, $CH_2OMe$, $CH_2OEt$, $CH_2OiPr$, $CH_2OnPr$, $CH_2OnBu$, $CH_2OtBu$, $CH_2OPh$, $C_2H_5OH$, $C_2H_5OMe$, $C_2H_5OEt$, $C_2H_5OiPr$, $C_2H_5OnPr$, $C_2H_5OnBu$, $C_2H_5OtBu$, $C_2H_5OPh$, OH, OMe, OEt, OnPr, OiPr, OnBu, OtBu, OPh, CHO, COMe, COEt, COnPr, COiPr, COnBu, COtBu, COPh, COCl, COBr, COI, COF, $COCF_3$, $COC_2F_5$, $COC_3F_7$, $CO_2H$, $CO_2Me$, $CO_2Et$, $CO_2nPr$, $CO_2iPr$, $CO_2nBu$, $CO_2tBu$, F, Cl, Br, I, $SO_2Me$, $SO_2Et$, $SO_2iPr$, $SO_2nPr$, $SO_2nBu$, $SO_2Bu$, $NH_2$, $N(OH)_2$, NHMe, NHEt, NHnPr, NHiPr, NHnBu, NHtBu, $N(Me)_2$, $N(Et)_2$, NMeEt, $N(nPr)_2$, $N(nBu)_2$, $N(tBu)_2$, $OSiMe_3$ or $OSiEt_3$, and/or $R_1$ or $R_2$ and $R_3$, or $R_{13}$ or $R_{14}$ and $R_{15}$, or $R_{25}$ or $R_{26}$ and $R_{27}$ each represent an unsubstituted or substituted sp3 hybridized carbon atom, whereas $R_1$ or $R_2$ and $R_3$, or $R_{13}$ or $R_{14}$ and $R_{15}$, or $R_{25}$ or $R_{26}$ and $R_{27}$ are interconnected directly or via a further unsubstituted or substituted sp3 hybridized carbon atom in such a manner that a five-membered ring or six-membered ring is formed, and/or $R_{14}$ represents a π-electron and $R_{13}$ and $R_{15}$ each represent an unsubstituted or substituted sp2 hybridized carbon atom, whereas $R_{13}$ and $R_{15}$ are interconnected via a further unsubstituted or substituted sp2 hybridized carbon atom in such a manner that an aromatic six-membered ring is formed, or $R_{26}$ represents a π-electron and $R_{25}$ and $R_{27}$ each represent an unsubstituted or substituted sp2 hybridized carbon atom, whereas $R_{25}$ and $R_{27}$ are interconnected via a further unsubstituted or substituted sp2 hybridized carbon atom in such a manner that an aromatic six-membered ring is formed, and/or $R_{14}$ represents a π-electron and $R_{13}$ represents an unsubstituted or substituted sp2 hybridized carbon atom and $R_{15}$ represents an unsubstituted or substituted nitrogen atom, whereas $R_{13}$ and $R_{15}$ are interconnected in such a manner that an aromatic five-membered ring is formed, or $R_{26}$ represents a π-electron and $R_{25}$ represents an unsubstituted or substituted sp2 hybridized carbon atom and $R_{27}$ represents a nitrogen atom, whereas $R_{25}$ and $R_{27}$ are interconnected in such a manner that an aromatic five-membered ring is formed, and/or $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each represent an unsubstituted or substituted sp2 hybridized carbon atom, whereas $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each are interconnected via two further unsubstituted or substituted sp2 hybridized carbon atoms in such a manner that an aromatic six-membered ring or two aromatic six-membered rings are formed, and $R_7$, $R_{19}$, $R_{31}$ represent hydrogen, and $R_1$ is unlike $R_2$.

In particular this further object of the present invention relates to cycloplatinated amineiodoplatinum(II) complexes of the general formula:

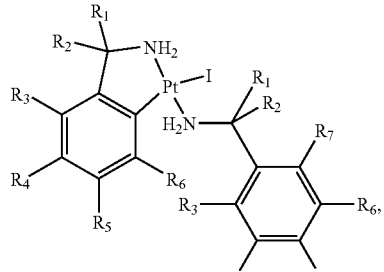

(IV)

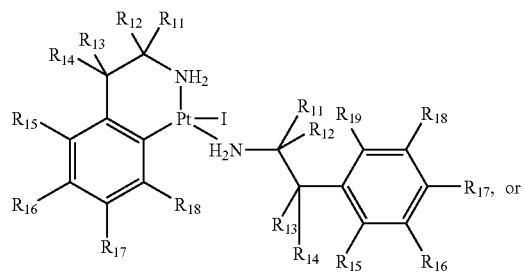

(V)

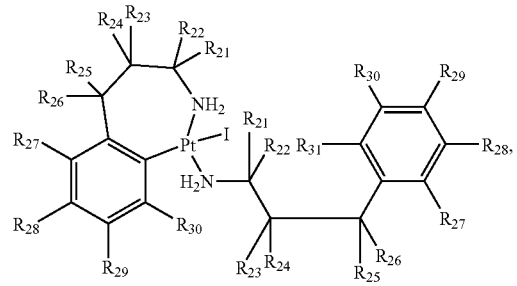

(VI)

whereas:
$R_1$-$R_6$, $R_{11}$-$R_{18}$, $R_{21}$-$R_{30}$ each independently of one another represent hydrogen or a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a silyl group having 1 to 10 carbon atoms, for example H, Me, Et, nPr, iPr, nBu, t-Bu, CMeEt, $C_6H_{11}$, $CF_3$, $C_2F_5$, Ph, $CH_2OH$, $CH_2OMe$, $CH_2OEt$, $CH_2OiPr$, $CH_2OnPr$, $CH_2OnBu$, $CH_2OtBu$, $CH_2OPh$, $C_2H_5OH$, $C_2H_5OMe$, $C_2H_5OEt$, $C_2H_5OiPr$, $C_2H_5OnPr$, $C_2H_5OnBu$, $C_2H_5OtBu$, $C_2H_5OPh$, OH, OMe, OEt, OnPr, OiPr, OnBu, OtBu, OPh, CHO, COMe, COEt, COnPr, COiPr, COnBu, COtBu, COPh, COCl, COBr, COI, COF, $COCF_3$, $COC_2F_5$, $COC_3F_7$, $CO_2H$, $CO_2Me$, $CO_2Et$, $CO_2nPr$, $CO_2iPr$, $CO_2nBu$, $CO_2tBu$, F, Cl, Br, I, $SO_2Me$, $SO_2Et$, $SO_2iPr$, $SO_2nPr$, $SO_2nBu$, $SO_2Bu$, $NH_2$, $N(OH)_2$, NHMe, NHEt, NHnPr, NHiPr, NHnBu, NHtBu, $N(Me)_2$, $N(Et)_2$, NMeEt, $N(nPr)_2$, $N(nBu)_2$, $N(tBu)_2$, $OSiMe_3$ or $OSiEt_3$, and/or $R_1$ or $R_2$ and $R_3$, or $R_{13}$ or $R_{14}$ and $R_{15}$, or $R_{25}$ or $R_{26}$ and $R_{27}$ each represent an unsubstituted or substituted sp3 hybridized carbon atom, whereas $R_1$ or $R_2$ and $R_3$, or $R_{13}$ or $R_{14}$ and $R_{15}$, or $R_{25}$ or $R_{26}$ and $R_{27}$ are interconnected directly or via a further unsubstituted or substituted sp3 hybridized carbon atom in such a manner that a five-membered ring or six-membered ring is formed, and/or $R_{14}$ represents a π-electron and $R_{13}$ and $R_{15}$ each represent an unsubstituted or substituted sp2 hybridized carbon atom, whereas $R_{13}$ and $R_{15}$ are interconnected via a further unsubstituted or substituted sp2 hybridized carbon atom in such a manner that an aromatic six-membered ring is formed, or $R_{26}$ represents a π-electron and $R_{25}$ and $R_{27}$ each represent an unsubstituted or substituted sp2 hybridized carbon atom, whereas $R_{25}$ and $R_{27}$ are interconnected via a further unsubstituted or substituted sp2 hybridized carbon atom in such a manner that an aromatic six-membered ring is formed, and/or $R_{14}$ represents a π-electron and $R_{13}$ represents an unsubstituted or substituted sp2 hybridized carbon atom and $R_{15}$ represents an unsubstituted or substituted nitrogen atom, whereas $R_{13}$ and $R_{15}$ are interconnected in such a manner that an aromatic five-membered ring is formed, or $R_{26}$ represents a π-electron and $R_{25}$ represents an unsubstituted or substituted sp2 hybridized carbon atom and $R_{27}$ represents a nitrogen atom, whereas $R_{25}$ and $R_{27}$ are interconnected in such a manner that an aromatic five-membered ring is formed, and/or $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each represent an unsubstituted or substituted sp2 hybridized carbon atom, whereas $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each are interconnected via two further unsubstituted or substituted sp2 hybridized carbon atoms in such a manner that an aromatic six-membered ring or two aromatic six-membered rings are formed, and $R_7$, $R_{19}$, $R_{31}$ represent hydrogen, and $R_1$ is unlike $R_2$.

A further object of the present invention relates to trans-bisamineplatinum(II) complexes, in particular trans-bisaminediiodoplatinum(II) complexes, of the general formula:

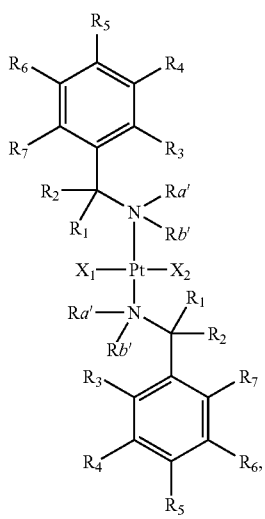

(vii)

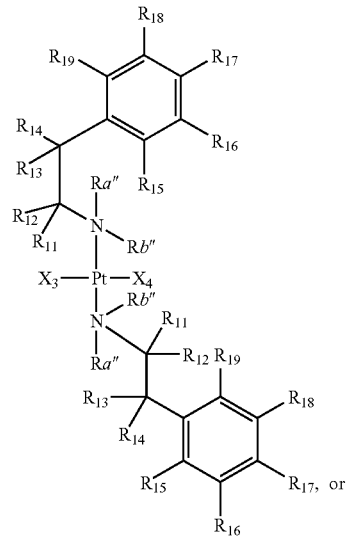

(viii)

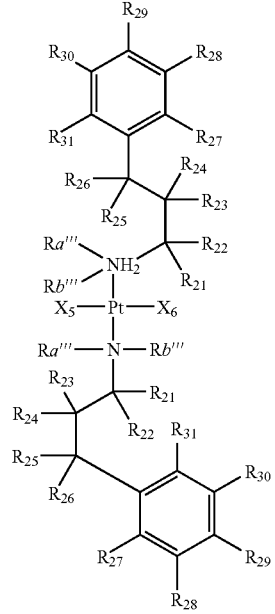

(ix)

whereas:

Ra', Rb', Ra", Rb", Ra'", Rb'" each independently of one another represent hydrogen or a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a nitroso group or a silyl group having 1 to 10 carbon atoms, for example H, Me, Et, nPr, iPr, nBu, t-Bu, CMeEt, $C_6H_{11}$, $CF_3$, $C_2F_5$, Ph, $CH_2OH$, $CH_2OMe$, $CH_2OEt$, $CH_2OiPr$, $CH_2OnPr$, $CH_2OnBu$, $CH_2OtBu$, $CH_2OPh$, $C_2H_5OH$, $C_2H_5OMe$, $C_2H_5OEt$, $C_2H_5OiPr$, $C_2H_5OnPr$, $C_2H_5OnBu$, $C_2H_5OtBu$, $C_2H_5OPh$, OH, OMe, OEt, OnPr, OiPr, OnBu, OtBu, OPh, CHO, COMe, COEt, COnPr, COiPr, COnBu, COtBu, COPh, COCl, COBr, COI, COF, $COCF_3$, $COC_2F_5$, $COC_3F_7$, $CO_2H$, $CO_2Me$, $CO_2Et$, $CO_2nPr$, $CO_2iPr$, $CO_2nBu$, $CO_2tBu$, F, Cl, Br, I, $SO_2Me$, $SO_2Et$, $SO_2iPr$, $SO_2nPr$, $SO_2nBu$, $SO_2Bu$, $NH_2$, NO, $NHCH_2Ph$, $OSiMe_3$ or $OSiEt_3$, and/or $R_1$-$R_6$, $R_{11}$-$R_{18}$, $R_{21}$-$R_{30}$ each independently of one another represent hydrogen or a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a silyl group having 1 to 10 carbon atoms, for example H, Me, Et, nPr, iPr, nBu, t-Bu, CMeEt, $C_6H_{11}$, $CF_3$, $C_2F_5$, Ph, $CH_2OH$, $CH_2OMe$, $CH_2OEt$, $CH_2OiPr$, $CH_2OnPr$, $CH_2OnBu$, $CH_2OtBu$, $CH_2OPh$, $C_2H_5OH$, $C_2H_5OMe$, $C_2H_5OEt$, $C_2H_5OiPr$, $C_2H_5OnPr$, $C_2H_5OnBu$, $C_2H_5OtBu$, $C_2H_5OPh$, OH, OMe, OEt, OnPr, OiPr, OnBu, OtBu, OPh, CHO, COMe, COEt, COnPr, COiPr, COnBu, COtBu, COPh, COCl, COBr, COI, COF, $COCF_3$, $COC_2F_5$, $COC_3F_7$, $CO_2H$, $CO_2Me$, $CO_2Et$, $CO_2nPr$, $CO_2iPr$, $CO_2nBu$, $CO_2tBu$, F, Cl, Br, I, $SO_2Me$, $SO_2Et$, $SO_2iPr$, $SO_2nPr$, $SO_2nBu$, $SO_2Bu$, $NH_2$, $N(OH)_2$, NHMe, NHEt, NHnPr, NHiPr, NHnBu, NHtBu, $N(Me)_2$, $N(Et)_2$, NMeEt, $N(nPr)_2$, $N(nBu)_2$, $N(tBu)_2$, $OSiMe_3$ or $OSiEt_3$, and/or $R_1$ or $R_2$ and $R_3$, or $R_{13}$ or $R_{14}$ and $R_{15}$, or $R_{25}$ or $R_{26}$ and $R_{27}$ each represent an unsubstituted or substituted sp3 hybridized carbon atom, whereas $R_1$ or $R_2$ and $R_3$, or $R_{13}$ or $R_{14}$ and $R_{15}$, or $R_{25}$ or $R_{26}$ and $R_{27}$ are interconnected directly or via a further unsubstituted or substituted sp3 hybridized carbon atom in such a manner that a five-membered ring or six-membered ring is formed, and/or $R_{14}$ represents a π-electron and $R_{13}$ and $R_{15}$ each represent an unsubstituted or substituted sp2 hybridized carbon atom, whereas $R_{13}$ and $R_{15}$ are interconnected via a further unsubstituted or substituted sp2 hybridized carbon atom in such a manner that an aromatic six-membered ring is formed, or $R_{26}$ represents a π-electron and $R_{25}$ and $R_{27}$ each represent an unsubstituted or substituted sp2 hybridized carbon atom, whereas $R_{25}$ and $R_{27}$ are interconnected via a further unsubstituted or substituted sp2 hybridized carbon atom in such a manner that an aromatic six-membered ring is formed, and/or $R_{14}$ represents a π-electron and $R_{13}$ represents an unsubstituted or substituted sp2 hybridized carbon atom and $R_{15}$ represents an unsubstituted or substituted nitrogen atom, whereas $R_{13}$ and $R_{15}$ are interconnected in such a manner that an aromatic five-membered ring is formed, or $R_{26}$ represents a π-electron and $R_{25}$ represents an unsubstituted or substituted sp2 hybridized carbon atom and $R_{27}$ represents a nitrogen atom, whereas $R_{25}$ and $R_{27}$ are interconnected in such a manner that an aromatic five-membered ring is formed, and/or $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each represent an unsubstituted or substituted sp2 hybridized carbon atom, whereas $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each are interconnected via two further unsubstituted or substituted sp2 hybridized carbon atoms in such a manner that an aromatic six-membered ring or two aromatic six-membered rings are formed, and $R_7$, $R_{19}$, $R_{31}$ represent hydrogen, and $R_1$ is unlike $R_2$, and $X_1$-$X_6$ each independently of one another represent a halogen atom, for example I, Cl, Br, F, or a pseudohalogen, for example NC, SCN, NCS, OCN, NCO, $N_3$, NCSe, or a $C_6F_5$ ligand or an unsubstituted or substituted, linear or branched alkylamine or an unsubstituted or substituted, linear or branched alkenylamine or an unsubstituted or substituted alkynylamine or an unsubstituted or substituted, linear or branched arylalkylamine, for example an amine of the general formula (i), (ii), (iii), in particular a primary amine of the general formula (I), (II) or (III), or a phosphane, for example $P(Ph)_3$, $P(C_6H_{11})_3$, $P(Me)_3$, $P(Et)_3$, $P(nPr)_3$, $P(iPr)_3$, $P(nBu)_3$, $P(tBu)_3$, $PCl_3$, $PF_3$, $PI_3$, $PBr_3$, or a N-heterocycle, for example pyridine, or a S-heterocycle, for example thiophene.

In particular this further object of the present invention relates to trans-bisamineplatinum(II) complexes, in particular trans-bisaminediiodoplatinum(II) complexes, of the general formula:

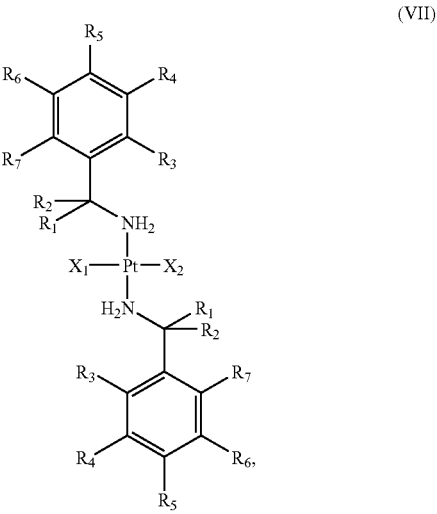

(VII)

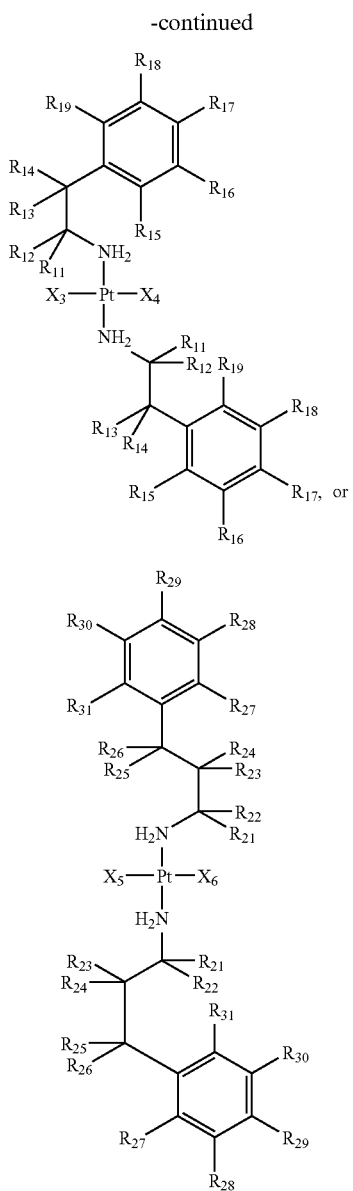

whereas:
$R_1$-$R_6$, $R_{11}$-$R_{18}$, $R_{21}$-$R_{30}$ each independently of one another represent hydrogen or a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a silyl group having 1 to 10 carbon atoms, for example H, Me, Et, nPr, iPr, nBu, t-Bu, CMeEt, $C_6H_{11}$, $CF_3$, $C_2F_5$, Ph, $CH_2OH$, $CH_2OMe$, $CH_2OEt$, $CH_2OiPr$, $CH_2OnPr$, $CH_2OnBu$, $CH_2OtBu$, $CH_2OPh$, $C_2H_5OH$, $C_2H_5OMe$, $C_2H_5OEt$, $C_2H_5OiPr$, $C_2H_5OnPr$, $C_2H_5OnBu$, $C_2H_5OtBu$, $C_2H_5OPh$, OH, OMe, OEt, OnPr, OiPr, OnBu, OtBu, OPh, CHO, COMe, COEt, COnPr, COiPr, COnBu, COtBu, COPh, COCl, COBr, COI, COF, $COCF_3$, $COC_2F_5$, $COC_3F_7$, $CO_2H$, $CO_2Me$, $CO_2Et$, $CO_2nPr$, $CO_2iPr$, $CO_2nBu$, $CO_2tBu$, F, Cl, Br, I, $SO_2Me$, $SO_2Et$, $SO_2iPr$, $SO_2nPr$, $SO_2nBu$, $SO_2Bu$, $NH_2$, $N(OH)_2$, NHMe, NHEt, NHnPr, NHiPr, NHnBu, NHtBu, $N(Me)_2$, $N(Et)_2$, NMeEt, $N(nPr)_2$, $N(nBu)_2$, $N(tBu)_2$, $OSiMe_3$ or $OSiEt_3$, and/or $R_1$ or $R_2$ and $R_3$, or $R_{13}$ or $R_{14}$ and $R_{15}$, or $R_{25}$ or $R_{26}$ and $R_{27}$ each represent an unsubstituted or substituted sp3 hybridized carbon atom, whereas $R_1$ or $R_2$ and $R_3$, or $R_{13}$ or $R_{14}$ and $R_{15}$, or $R_{25}$ or $R_{26}$ and $R_{27}$ are interconnected directly or via a further unsubstituted or substituted sp3 hybridized carbon atom in such a manner that a five-membered ring or six-membered ring is formed, and/or $R_{14}$ represents a π-electron and $R_{13}$ and $R_{15}$ each represent an unsubstituted or substituted sp2 hybridized carbon atom, whereas $R_{13}$ and $R_{15}$ are interconnected via a further unsubstituted or substituted sp2 hybridized carbon atom in such a manner that an aromatic six-membered ring is formed, or $R_{26}$ represents a π-electron and $R_{25}$ and $R_{27}$ each represent an unsubstituted or substituted sp2 hybridized carbon atom, whereas $R_{25}$ and $R_{27}$ are interconnected via a further unsubstituted or substituted sp2 hybridized carbon atom in such a manner that an aromatic six-membered ring is formed, and/or $R_{14}$ represents a π-electron and $R_{13}$ represents an unsubstituted or substituted sp2 hybridized carbon atom and $R_{15}$ represents an unsubstituted or substituted nitrogen atom, whereas $R_{13}$ and $R_{15}$ are interconnected in such a manner that an aromatic five-membered ring is formed, or $R_{26}$ represents a π-electron and $R_{25}$ represents an unsubstituted or substituted sp2 hybridized carbon atom and $R_{27}$ represents a nitrogen atom, whereas $R_{25}$ and $R_{27}$ are interconnected in such a manner that an aromatic five-membered ring is formed, and/or $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each represent an unsubstituted or substituted sp2 hybridized carbon atom, whereas $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each are interconnected via two further unsubstituted or substituted sp2 hybridized carbon atoms in such a manner that an aromatic six-membered ring or two aromatic six-membered rings are formed, and $R_7$, $R_{19}$, $R_{31}$ represent hydrogen, and
$R_1$ is unlike $R_2$, and
$X_1$-$X_6$ each independently of one another represent a halogen atom, for example I, Cl, Br, F, or a pseudohalogen, for example NC, SCN, NCS, OCN, NCO, $N_3$, NCSe, or a $C_6F_5$ ligand or an unsubstituted or substituted, linear or branched alkylamine or an unsubstituted or substituted, linear or branched alkenylamine or an unsubstituted or substituted alkynylamine or an unsubstituted or substituted, linear or branched arylalkylamine, for example a primary amine of the general formula (I), (II) or (III), or a phosphane, for example $P(Ph)_3$, $P(C_6H_{11})_3$, $P(Me)_3$, $P(Et)_3$, $P(nPr)_3$, P(iPr)$_3$, P(nBu)$_3$, P(tBu)$_3$, PCl$_3$, PF$_3$, PI$_3$, PBr$_3$, or a N-heterocycle, for example pyridine, or a S-heterocycle, for example thiophene.

A further object of the present invention relates to cycloplatinated platinum(II) complexes of the general formula:

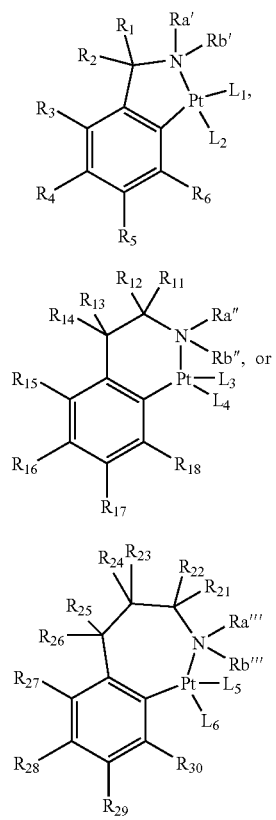

(x)

(xi)

(xii)

whereas:

Ra', Rb', Ra", Rb", Ra''', Rb''' each independently of one another represent hydrogen or a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a nitroso group or a silyl group having 1 to 10 carbon atoms, for example H, Me, Et, nPr, iPr, nBu, t-Bu, CMeEt, C$_6$H$_{11}$, CF$_3$, C$_2$F$_5$, Ph, CH$_2$OH, CH$_2$OMe, CH$_2$OEt, CH$_2$OiPr, CH$_2$OnPr, CH$_2$OnBu, CH$_2$OtBu, CH$_2$OPh, C$_2$H$_5$OH, C$_2$H$_5$OMe, C$_2$H$_5$OEt, C$_2$H$_5$OiPr, C$_2$H$_5$OnPr, C$_2$H$_5$OnBu, C$_2$H$_5$OtBu, C$_2$H$_5$OPh, OH, OMe, OEt, OnPr, OiPr, OnBu, OtBu, OPh, CHO, COMe, COEt, COnPr, COiPr, COnBu, COtBu, COPh, COCl, COBr, COI, COF, COCF$_3$, COC$_2$F$_5$, COC$_3$F$_7$, CO$_2$H, CO$_2$Me, CO$_2$Et, CO$_2$nPr, CO$_2$iPr, CO$_2$nBu, CO$_2$tBu, F, Cl, Br, I, SO$_2$Me, SO$_2$Et, SO$_2$iPr, SO$_2$nPr, SO$_2$nBu, SO$_2$Bu, NH$_2$, NO, NHCH$_2$Ph, OSiMe$_3$ or OSiEt$_3$, and/or R$_1$-R$_6$, R$_{11}$-R$_{18}$, R$_{21}$-R$_{30}$ each independently of one another represent hydrogen or a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a silyl group having 1 to 10 carbon atoms, for example H, Me, Et, nPr, iPr, nBu, t-Bu, CMeEt, C$_6$H$_{11}$, CF$_3$, C$_2$F$_5$, Ph, CH$_2$OH, CH$_2$OMe, CH$_2$OEt, CH$_2$OiPr, CH$_2$OnPr, CH$_2$OnBu, CH$_2$OtBu, CH$_2$OPh, C$_2$H$_5$OH, C$_2$H$_5$OMe, C$_2$H$_5$OEt, C$_2$H$_5$OiPr, C$_2$H$_5$OnPr, C$_2$H$_5$OnBu, C$_2$H$_5$OtBu, CH$_2$OPh, C$_2$H$_5$OH, OEt, OnPr, OiPr, OnBu, OtBu, OPh, CHO, COMe, COEt, COnPr, COiPr, COnBu, COtBu, COPh, COLI, COBr, COI, COF, COCF$_3$, COC$_2$F$_5$, COC$_3$F$_7$, CO$_2$H, CO$_2$Me, CO$_2$Et, CO$_2$nPr, CO$_2$iPr, CO$_2$nBu, CO$_2$tBu, F, Cl, Br, I, SO$_2$Me, SO$_2$Et, SO$_2$iPr, SO$_2$nPr, SO$_2$nBu, SO$_2$Bu, NH$_2$, N(OH)$_2$, NHMe, NHEt, NHnPr, NHiPr, NHnBu, NHtBu, N(Me)$_2$, N(Et)$_2$, NMeEt, N(nPr)$_2$, N(nBu)$_2$, N(tBu)$_2$, OSiMe$_3$ or OSiEt$_3$, and/or R$_1$ or R$_2$ and R$_3$, or R$_{13}$ or R$_{14}$ and R$_{15}$, or R$_{25}$ or R$_{26}$ and R$_{27}$ each represent an unsubstituted or substituted sp3 hybridized carbon atom, whereas R$_1$ or R$_2$ and R$_3$, or R$_{13}$ or R$_{14}$ and R$_{15}$, or R$_{25}$ or R$_{26}$ and R$_{27}$ are interconnected directly or via a further unsubstituted or substituted sp3 hybridized carbon atom in such a manner that a five-membered ring or six-membered ring is formed, and/or R$_{14}$ represents a π-electron and R$_{13}$ and R$_{15}$ each represent an unsubstituted or substituted sp2 hybridized carbon atom, whereas R$_{13}$ and R$_{15}$ are interconnected via a further unsubstituted or substituted sp2 hybridized carbon atom in such a manner that an aromatic six-membered ring is formed, or R$_{26}$ represents a π-electron and R$_{25}$ and R$_{27}$ each represent an unsubstituted or substituted sp2 hybridized carbon atom, whereas R$_{25}$ and R$_{27}$ are interconnected via a further unsubstituted or substituted sp2 hybridized carbon atom in such a manner that an aromatic six-membered ring is formed, and/or R$_{14}$ represents a π-electron and R$_{13}$ represents an unsubstituted or substituted sp2 hybridized carbon atom and R$_{15}$ represents an unsubstituted or substituted nitrogen atom, whereas R$_{13}$ and R$_{15}$ are interconnected in such a manner that an aromatic five-membered ring is formed, or R$_{26}$ represents a π-electron and R$_{25}$ represents an unsubstituted or substituted sp2 hybridized carbon atom and R$_{27}$ represents a nitrogen atom, whereas $R_{25}$ and $R_{27}$ are interconnected in such a manner that an aromatic five-membered ring is formed, and/or $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each represent an unsubstituted or substituted sp2 hybridized carbon atom, whereas $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each are interconnected via two further unsubstituted or substituted sp2 hybridized carbon atoms in such a manner that an aromatic six-membered ring or two aromatic six-membered rings are formed, and $R_1$ is unlike $R_2$, and $L_1$-$L_6$ each independently of one another represent a halogen atom, for example I, Cl, Br, F, or a pseudohalogen, for example NC, SCN, NCS, OCN, NCO, $N_3$, NCSe, or a $C_6F_5$ ligand or an unsubstituted or substituted, linear or branched alkylamine or an unsubstituted or substituted, linear or branched alkenylamine or an unsubstituted or substituted alkynylamine or an unsubstituted or substituted, linear or branched arylalkylamine, for example an amine of the general formula (i), (ii), (iii), in particular a primary amine of the general formula (I), (II) or (III), or a phosphane, for example $P(Ph)_3$, $P(C_6H_{11})_3$, $P(Me)_3$, $P(Et)_3$, $P(nPr)_3$, $P(iPr)_3$, $P(nBu)_3$, $P(tBu)_3$, $PCl_3$, $PF_3$, $PI_3$, $PBr_3$, or a N-heterocycle, for example pyridine, or a S-heterocycle, for example thiophene, or $L_1$ and $L_2$, or $L_3$ and $L_4$, or $L_5$ and $L_6$ represent a chelate ligand, for example a bis(dialkylphosphino)alkane, bis(diphenylphosphino)alkane, bis(dialkylphosphino)alkene, bis(diphenylphosphino)alkene, an alkylene diamine, an oxalate, 2,2'-bis(diphenylphosphino)-1,1'-binaphthyl (BINAP), ethanolamine(2-amineoethanol), thioethanolamine(2-aminoethanethiol), 1,1'-bis(diphenyl)phosphinoferrocene, 2-piperidylmethanol, glycerine, glycolic acid, 1,2-diaminocyclohexane, malonic acid, tetramethylethylenediamine, ethylenediaminetetraacetic acid, N,N'-ribavirin (1-beta-D-ribofuranosyl-1, 2,4-triazol-3-carboxamide), acetylacetonate or 2,2'-bipyridine.

In particular this further object of the present invention relates to cycloplatinated platinum(II) complexes of the general formula:

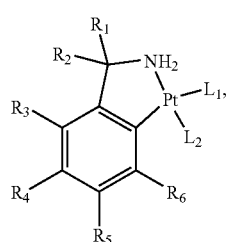
(X)

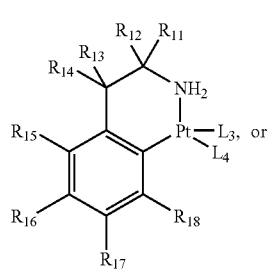
(XI)

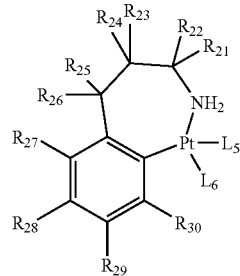
(XII)

whereas:

$R_1$-$R_6$, $R_{11}$-$R_{18}$, $R_{21}$-$R_{30}$ each independently of one another represent hydrogen or a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a silyl group having 1 to 10 carbon atoms, for example H, Me, Et, nPr, iPr, nBu, t-Bu, CMeEt, $C_6H_{11}$, $CF_3$, $C_2F_5$, Ph, $CH_2OH$, $CH_2OMe$, $CH_2OEt$, $CH_2OiPr$, $CH_2OnPr$, $CH_2OnBu$, $CH_2OtBu$, $CH_2OPh$, $C_2H_5OH$, $C_2H_5OMe$, $C_2H_5OEt$, $C_2H_5OiPr$, $C_2H_5OnPr$, $C_2H_5OnBu$, $C_2H_5OtBu$, $C_2H_5OPh$, OH, OMe, OEt, OnPr, OiPr, OnBu, OtBu, OPh, CHO, COMe, COEt, COnPr, COiPr, COnBu, COtBu, COPh, COCl, COBr, COI, COF, $COCF_3$, $COC_2F_5$, $COC_3F_7$, $CO_2H$, $CO_2Me$, $CO_2Et$, $CO_2nPr$, $CO_2iPr$, $CO_2nBu$, $CO_2tBu$, F, Cl, Br, I, $SO_2Me$, $SO_2Et$, $SO_2iPr$, $SO_2nPr$, $SO_2nBu$, $SO_2Bu$, $NH_2$, $N(OH)_2$, NHMe, NHEt, NHnPr, NHiPr, NHnBu, NHtBu, $N(Me)_2$, $N(Et)_2$, NMeEt, $N(nPr)_2$, $N(nBu)_2$, $N(tBu)_2$, $OSiMe_3$ or $OSiEt_3$, and/or $R_1$ or $R_2$ and $R_3$, or $R_{13}$ or $R_{14}$ and $R_{15}$, or $R_{25}$ or $R_{26}$ and $R_{27}$ each represent an unsubstituted or substituted sp3 hybridized carbon atom, whereas $R_1$ or $R_2$ and $R_3$, or $R_{13}$ or $R_{14}$ and $R_{15}$, or $R_{25}$ or $R_{26}$ and $R_{27}$ are interconnected directly or via a further unsubstituted or substituted sp3 hybridized carbon atom in such a manner that a five-membered ring or six-membered ring is formed, and/or $R_{14}$ represents a π-electron and $R_{13}$ and $R_{15}$ each represent an unsubstituted or substituted sp2 hybridized carbon atom, whereas $R_{13}$ and $R_{15}$ are interconnected via a further unsubstituted or substituted sp2 hybridized carbon atom in such a manner that an aromatic six-membered ring is formed, or $R_{26}$ represents a π-electron and $R_{25}$ and $R_{27}$ each represent an unsubstituted or substituted sp2 hybridized carbon atom, whereas $R_{25}$ and $R_{27}$ are interconnected via a further unsubstituted or substituted sp2 hybridized carbon atom in such a manner that an aromatic six-membered ring is formed, and/or $R_{14}$ represents a π-electron and $R_{13}$ represents an unsubstituted or substituted sp2 hybridized carbon atom and $R_{15}$ represents an unsubstituted or substituted nitrogen atom, whereas $R_{13}$ and $R_{15}$ are interconnected in such a manner that an aromatic five-membered ring is formed, or $R_{26}$ represents a π-electron and $R_{25}$ represents an unsubstituted or substituted sp2 hybridized carbon atom and $R_{27}$ represents a nitrogen atom, whereas $R_{25}$ and $R_{27}$ are interconnected in such a manner that an aromatic five-membered ring is formed, and/or $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each represent an unsubstituted or substituted sp2 hybridized carbon atom, whereas $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each are interconnected via two further unsubstituted or substituted sp2 hybridized carbon atoms in such a manner that an aromatic six-membered ring or two aromatic six-membered rings are formed, and $R_1$ is unlike $R_2$, and $L_1$-$L_6$ each independently of one another represent a halogen atom, for example I, Cl, Br, F, or a pseudohalogen, for example NC, SCN, NCS, OCN, NCO, $N_3$, NCSe, or a $C_6F_5$ ligand or an unsubstituted or substituted, linear or branched alkylamine or an unsubstituted or substituted, linear or branched alkenylamine or an unsubstituted or substituted alkynylamine or an unsubstituted or substituted, linear or branched arylalkylamine, for example a primary amine of the general formula (I), (II) or (III), or a phosphane, for example $P(Ph)_3$, $P(C_6H_{11})_3$, $P(Me)_3$, $P(Et)_3$, $P(nPr)_3$, $P(iPr)_3$, $P(nBu)_3$, $P(tBu)_3$, $PCl_3$, $PF_3$, $PI_3$, $PBr_3$, or a N-heterocycle, for example pyridine, or a S-heterocycle, for example thiophene, or $L_1$ and $L_2$, or $L_3$ and $L_4$, or $L_5$ and $L_6$ represent a chilate ligand, for example a bis(dialkylphosphino)alkane, bis(diphenylphosphino)alkane, bis(dialkylphosphino)alkene, bis(diphenylphosphino)alkene, an alkylene diamine, an oxalate, 2,2'-bis(diphenylphosphino)-1,1'-binaphthyl (BINAP), ethanolamine(2-amineoethanol), thioethanolamine(2-aminoethanethiol), 1,1'-bis(diphenyl)phosphinoferrocene, 2-piperidylmethanol, glycerine, glycolic acid, 1,2-diaminocyclohexane, malonic acid, tetramethylethylenediamine, ethylenediaminetetraacetic acid, N,N'-ribavirin(1-beta-D-ribofuranosyl-1,2,4-triazol-3-carboxamide), acetylacetonate or 2,2'-bipyridine.

Preferably compounds prepared in the context of the process according to the invention, for example of the general formula iv to xii and/or IV to XII, have at least one chiral carbon atom. For example, compounds prepared in the context of the process according to the invention have, for instance of the general formula iv to xii and/or IV to XII, have an amine group, which is connected via at least one chiral carbon atom to an aromatic group. Therefore, in the context of a preferred embodiment of the invention $R_1$ is unlike $R_2$, or $R_{11}$ is unlike $R_{12}$ and/or $R_{13}$ is unlike $R_{14}$, or $R_{21}$ is unlike $R_{22}$ and/or $R_{23}$ is unlike $R_{24}$ and/or $R_{25}$ is unlike $R_{26}$.

A further object of the present invention relates to the use of a platinum complex according to the invention of the general formula iv to xii and/or IV to XII or of a platinum complex obtainable by the process according to the invention for the treatment of tumor diseases and/or hemo blastoses, for example for the treatment of leukemia, in particular acute myeloid leukemia and/or multiple myeloma.

An other object of the present invention relates to the use of a platinum complex according to the invention of the general formula iv to xii and/or IV to XII or of a platinum complex obtainable by the process according to the invention for the preparation of a drug.

A particular advantage of the platinum complexes according to the invention is based on the fact that the complexes can excellently, sterically and electronically be adapted, since the complexes can simply be modified with a wide variety of alternatives.

A further object of the present invention relates to the use of a platinum complex according to the invention of the general formula iv to xii and/or IV to XII or of a platinum complex obtainable by the process according to the invention as catalyst or for the preparation of a catalyst.

Examples illustrating the present invention are given below.

EXAMPLES

1. First Process Step: Synthesis of the Iodoplatinum Precursor 415 mg (1 mmol) potassium tetrachloroplatinate were dissolved in 5 ml of water. To this solution 0.528 ml (4 mmol) hydroiodic acid (57%) were added. Subsequently, the solution was stirred for 2 hours at room temperature. After evaporation of the water, the iodoplatinum precursor was obtained in quantitative yield.

The iodoplatinum precursor was analyzed by x-ray powder diffraction. The powder diffractogram comprised apart from some lines assignable to potassium tetraiodoplatinate further lines. Some of these lines match with a powder diffractogram calculated on the basis of the single crystal structure of $K_2PtI_5$, which was determined by Thiele et al. (Thiele, G.; Mrozek, C.; Wittmann, K.; Wirkner, H. Naturwissenschaften 1978, 65, 206). The iodoplatinum precursor therefore comprises a mixture of at least two crystalline substances.

2.1. Second Process Step: Synthesis of (S,S)—PtI(4-R—$C_6H_3$CHMeNH$_2$)(H$_2$NCHMeC$_6H_4$-4-R)

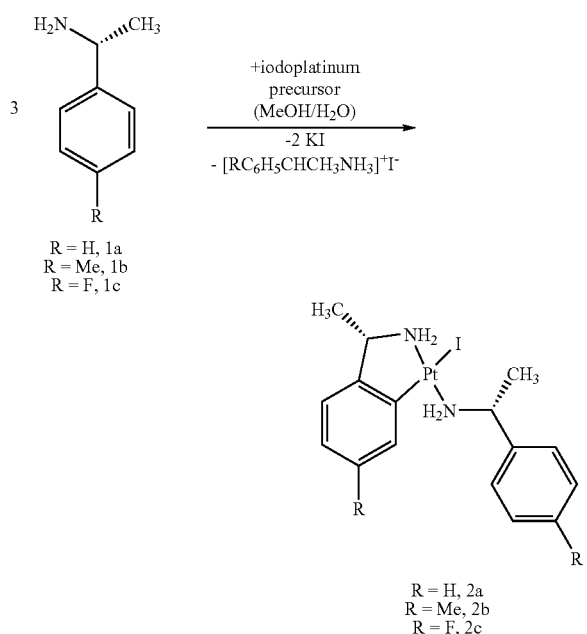

The reactions explained in detail below, show that the reaction is accelerated by an electron-releasing substituent (2b) on the benzyl ring and is slowed down by an electron-withdrawing substituents (2c) on the benzyl ring, whereas the yield is not detrimentally effected. This shows that the process according to the invention can successfully be carried out with extremely different substituents on the benzyl ring.

2.1.1 Synthesis of (S,S)—PtI(C$_6$H$_4$CHMeNH$_2$) (H$_2$NCHMeC$_6$H$_5$) (2a)

For synthesizing (S,S)—PtI(C$_6$H$_4$CHMeNH$_2$) (H$_2$NCHMeC$_6$H$_5$) (2a), 1 mmol of the iodoplatinum precursor obtained in the first process step was suspended in 30 ml of a MeOH/H$_2$O-mixture (2:1 v/v). Subsequently, 4 mmol of the ligand 1a were added and the reaction mixture was heated for four hours to reflux. The color of the reaction mixture changed from brown over yellow to a white solid. After cooling the reaction mixture, the solid was filtered off and washed with a cold MeOH/H$_2$O-mixture (2:1 v/v). The filtered solid yielded 86%. By treatment of the filtrate, the yield could be increased to 95%.

NMR: $^1$H-NMR (400 MHz, C$_6$D$_6$): δ=0.93 (d, 3H, J=6.56 Hz, CHMe cycloplatinated amine); 1.58 (d, 3H, J=6.80 Hz, CHMe non-cycloplatinated amine); 3.09, 3.44 (br, 2H, NH$_2$, non-cycloplatinated amine); 3.26, 5.23 (br, 2H, NH$_2$, cycloplatinated amine); (3.74 (m, 1H, CH, cycloplatinated amine); 4.13 (m, 1H, CH, non-cycloplatinated amine); 6.63, 6.74 (m, 2H, H4, H5); 6.64, 6.66 (m, 2H, H2, H3); 6.86 (m, 1H, H10); 7.02 (m, 2H, H8, H12); 7.03 (m, 2H, H4, H11) ppm. $^{13}$C-NMR (100.6 MHz, C$_6$D$_6$): δ=23.00 (s, 1C, CH$_3$, non-cycloplatinated amine); 24.06 (s, 1C, CH$_3$, cycloplatinated amine); 58.39 (s, 1C, CH, non-cycloplatinated amine); 62.96 (s, 1C, CH, cycloplatinated amine); 121.22, 128.19 (s, 2C, C4, C5); 123.64, 125.22 (s, 2C, C2, C3); 126.36 (s, 1C, C10); 127.92 (s, 2C, C8, C12); 128.46 (s, 2C, C9, C11); 139.81 (s, 1C, C6); 143.18 (s, 1C, C7); 155.20 (s, 1C, C1) ppm. $^{195}$Pt-NMR (107.4 MHz, C$_6$D$_6$): δ=−3302.81 ppm. Micro analysis: H: 3.76, C: 34.11, N: 4.97 (calculated), H: 4.50, C: 34.22, N: 4.81 (measured).

Furthermore the molecular structure of (S,S)—PtI(C$_6$H$_4$CHMeNH$_2$)(H$_2$NCHMeC$_6$H$_5$) (2a) was determined by single crystal x-ray structure analysis (see FIG. 1). For clarity reasons, only the hydrogen atom bound to the chiral center is shown in FIG. 1. In (S,S)—PtI(C$_6$H$_4$CHMeNH$_2$)—(H$_2$NCHMeC$_6$H$_5$) (2a), the platinum-nitrogen bond length of the cycloplatinated amine ligand is shorter than the platinum-nitrogen bond length of the monodentate bond amine ligand.

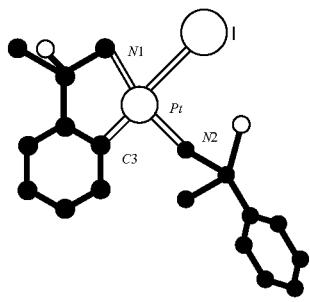

FIG. 1: Molecular Structure of (S,S)—PtI (C$_6$H$_4$CHMeNH$_2$)(H$_2$NCHMeC$_6$H$_5$) (2a) Determined by Single Crystal X-Ray Structure Analysis Selected bond length and angles of (S,S)—PtI (C$_6$H$_4$CHMeNH$_2$)(H$_2$NCHMeC$_6$H$_5$) (2a): Pt—C3 2.028(15), Pt—N1 2.050(13), Pt—N2 2.077(13), Pt—I 2.7087(12) Å, C3-Pt—I 175.0(4), N1-Pt—N2 176.3(5)°.

2.1.2 Synthesis of (S,S)—PtI(4-Me-C$_6$H$_3$CHMeNH$_2$)(H$_2$NCHMeC$_6$H$_4$-4-Me) (2b)

For synthesizing (S,S)—PtI(4-Me-C$_6$H$_3$CHMeNH$_2$) (H$_2$NCHMeC$_6$H$_4$-4-Me) (2b), 1 mmol of the iodoplatinum precursor obtained in the first process step was suspended in 30 ml of a MeOH/H$_2$O-mixture (2:1 v/v). Subsequently, 4 mmol of the ligand 1b were added and the reaction mixture was heated less than three hours to reflux. Thereby, the color of the reaction mixture changed from brown over yellow to a white solid. After cooling the reaction mixture, the solid was filtered off and washed with a cold MeOH/H2O-mixture (2:1 v/v). The filtered solid yielded 87.5%. By treatment of the filtrate, the yield could be increased to 95%.

NMR: $^1$H-NMR (400 MHz, C$_6$D$_6$): δ=0.99 (d, 3H, J=6.60 Hz, CHMe cycloplatinate amine); 1.60 (d, 3H, J=6.76 Hz, CHMe non-cycloplatinated amine); 1.87 (s, 3H, 4-Me(Ph) cycloplatinated amine); 2.09 (s, 3H, 4-Me(Ph) non-cycloplatinated amine); 2.61 (br, 1H, NH, non-cycloplatinated amine); 3.35 (br, 2H, NH non-cycloplatinated and NH cycloplatinated amine); 4.00 (m, 2H, CH, non-cycloplatinated and cycloplatinated amine); 6.06 (br, 1H, NH, cycloplatinated amine); 6.39 (s, 1H, H5); 6.42 (d, 1H, J=7.60 Hz, H3); 6.61 (d, 1H, J=7.56 Hz, H2); 6.69 (d, 2H, J=8.00 Hz, H8, H12); 6.87 (d, 2H, J=7.80 Hz, H9, H11) ppm. $^{13}$CNMR (100.6 MHz, C$_6$D$_6$): δ=21.08 (s, 2C, 4-CH$_3$(Ph), non-cycloplatinated and cycloplatinated amine); 23.45 (s, 1C, CH$_3$, non-cycloplatinated amine); 24.65 (s, 1C, CH$_3$, cycloplatinated amine); 58.53 (s, 1C, CH, non-cycloplatinated amine); 62.57 (s, 1C, CH, cycloplatinated amine); 120.63, (s, 1C, C2); 124.34 (s, 1C, C3); 126.15 (s, 2C, C8, C12); 129.54 (s, 1C, C5); 129.68 (s, 2C, C9, C11); 133.91 (s, 1C, C4); 137.70 (s, 1C, C10); 140.00 (s, 1C, C6); 141.00 (s, 1C, C7); 153.11 (s, 1C, C1) ppm. $^{195}$Pt-NMR (107.4 MHz, C$_6$D$_6$): δ=−3297.59 ppm. Micro analysis: H: 4.26, C: 36.56, N: 4.74 (calculated), H: 4.30, C: 35.77, N: 4.65 (measured).

2.1.3 Synthesis of (S,S)—PtI(4-F—C$_6$H$_3$CHMeNH$_2$)(H$_2$NCHMeC$_6$H$_4$-4-F) (2c)

For synthesizing (S,S)—PtI(4-F—C$_6$H$_3$CHMeNH$_2$) (H$_2$NCHMeC$_6$H$_4$-4-F) (2c), 1 mmol of the iodoplatinum precursor obtained in the first process step was suspended in 30 ml of a MeOH/H2O-mixture (2:1 v/v). Subsequently, 4 mmol of the ligand 1c were added and the reaction mixture was heated to reflux over night. Thereby, the color of the reaction mixture changed from brown over yellow to a white solid. After cooling the reaction mixture, the solid was filtered off and washed with a cold MeOH/H2O-mixture (2:1 v/v). The filtered solid yielded 94%. By treatment of the filtrate, the yield could be increased to 95%.

NMR: $^1$H-NMR (400 MHz, CD$_2$Cl$_2$): δ=1.46 (d, 3H, J=6.60 Hz, CHMe cycloplatinated amine); 1.60 (d, 3H, J=6.59 Hz, CHMe non-cycloplatinated amine); 3.64 (br, 2H, NH non-cycloplatinated and NH cycloplatinated amine); 3.79 (br, 2H, NH, amine, non-cycloplatinated amine); 4.24 (m, 1H, CH, cycloplatinated amine); 4.46 (m, 1H, CH, non-cycloplatinated amine); 4.64 (br, 1H, NH, amine, cycloplatinated amine); 6.36 (s, 1H, H5); 6.66 (m, 1H, H3); 6.91 (m, 1H, H2); 7.09 (m, 2H, H8, H12); 7.38 (m, 2H, H9, H11) ppm. HC-NMR (100.6 MHz, CD$_2$Cl$_2$): δ=22.91 (s, 1C, CH 3, non-cycloplatinated amine); 24.25 (s, 1C, CH$_3$, cycloplatinated amine) 57.98 (s, 1C, CH, non-cycloplatinated amine); 62.89 (s, 1C, CH, cycloplatinated amine); 110.22, (d, 1C, JC—F=21.40 Hz, C3); 114.79 (d, 1C, JC—F=18.72 Hz, C5); 116.27 (d, 2C, JC—F=20.06 Hz, C8, C12); 122.83 (d, 1C, JC—F=8.03 Hz, C2); 128.78 (d, 2C, JC—F=7.46 Hz, C9, C11); 138.66 (s, 1C, C7); 141.84 (s, 1C, C6); 149.82 (s, 1C, C1); 160.20 (d, 1C, JC—F=246.53 Hz, C4); 163.04 (d, 1C, JC—F=246.53, C10) ppm. $^{19}$F-NMR (376.3 MHz, CD$_2$Cl$_2$): −114.07 (m, 1F, non-cycloplatinated amine); −116.70 (m, 1F, cycloplatinated amine). $^{195}$Pt-NMR (107.4 MHz, CD$_2$Cl$_2$): δ=−3315.87 ppm. Micro analysis: H: 3.20, C: 32.07, N: 4.67 (calculated), H: 3.30, C: 31.99, N: 4.61 (measured).

Moreover, the molecular structure of (S,S)—PtI(4-F—C$_6$H$_3$CHMeNH$_2$)(H$_2$NCHMeC$_6$H$_4$-4-F) (2c) was determined by single crystal x-ray structure analysis (see FIG. 2). For clarity reasons, also in FIG. 2, only the hydrogen atom bound to the chiral center is shown. Although, cycloplatination is slower in the case of electron-withdrawing substituents on the benzyl moiety, as explained above, and the crystal structures of (S,S)—PtI(4-F—C$_6$H$_3$CHMeNH$_2$)(H$_2$NCHMeC$_6$H$_4$-4-F) (2c) and (S,S)—PtI(C$_6$H$_4$CHMeNH$_2$)(H$_2$NCHMeC$_6$H$_5$) (2a) are not isomorphous, the molecular structures of both compounds are quite similar.

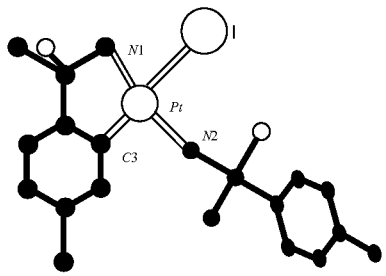

FIG. 2: Molecular Structure of (S,S)—PtI(4-F—C$_6$H$_3$CHMeNH$_2$)(H$_2$NCHMeC$_6$H$_4$-4-F) (2c) Determined by Single Crystal X-Ray Structure Analysis Selected bond length and angles of PtI(4-F—C$_6$H$_3$CHMeNH$_2$)(H$_2$NCHMeC$_6$H$_4$-4-F) (2c): Pt—C3 1.986(9), Pt—N1 2.035(8), Pt—N2 2.056(8), Pt—I 2.6878(10) Å, C3-Pt—I 173.8(3), N1-Pt—N2 179.4(3)°.

2.2. Second Process Step: Synthesis of (S,S)-trans-PtI$_2$(H$_2$NCHMeC$_6$H$_4$—R)$_2$

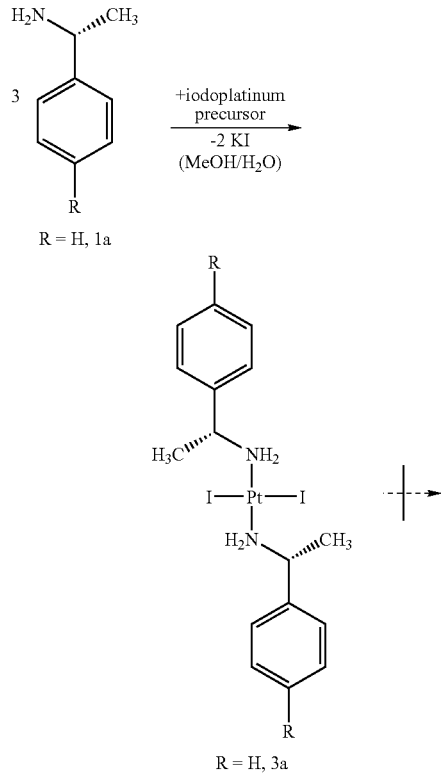

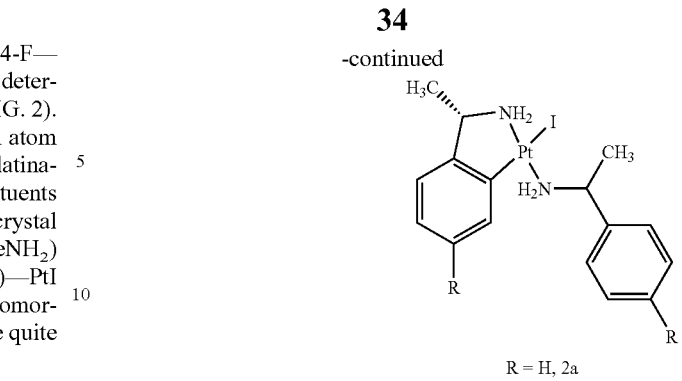

R = H, 2a 2.2.1 Synthesis of (S,S)-trans-PtI$_2$(H$_2$NCHMeC$_6$H$_5$)$_2$ (3a)

In the context of the present invention, it was found that the trans-diaminediiodo substituted intermediate 3a of the reaction described under item 2.1 can be obtained in a quantitative manner by halting the reaction after a short reaction time—compared with the reaction time of 2a of 4 hours—of about 30 minutes. For example by concentrating the reaction mixture, the desired intermediate 3a can be obtained as light yellow microcrystalline solid.

NMR: $^1$H-NMR (400 MHz, CD$_2$Cl$_2$): δ=1.71 (d, 6H, J=6.92 Hz, CHMe); 3.50-3.90 (br, 4H, NH$_2$); 4.50 (m, 2H, CHMe); 7.29-7.40 (m, 10H, H2-H6) ppm. $^{13}$C-NMR (100.6 MHz, CD$_2$Cl$_2$): δ=21.60 (s, 2C, CH$_3$); 57.79 (s, 2C, CH); 127.71, 128.27 (s, 10C, C2-C6), 141.32 (s, 2C, C1) ppm. $^{195}$Pt-NMR (107.4 MHz, CD$_2$Cl$_2$): δ=−3354.21 ppm. Micro analysis: H: 3.18, C: 27.77, N: 4.05 (calculated), H: 3.19, C: 27.79, N: 4.02 (measured).

In the context of the present invention, also the molecular structure of the intermediate (S,S)-trans-PtI$_2$(H$_2$NCHMeC$_6$H$_5$)$_2$ (3a) could be determined by single crystal x-ray structure analysis (see FIG. 3). For clarity reasons, also in FIG. 3, only the hydrogen atom bound to the chiral center is shown. Die crystal structure of (S,S)-trans-PtI$_2$(H$_2$NCHMeC$_6$H$_5$)$_2$ (3a) comprises six symmetrically independent square-planar platinum complex molecules, which mainly differ by their conformation. The platinum-iodine bond lengths or rather the platinum-nitrogen bond lengths are thereby in a range of 2.6009(10) to 2.6199(8) Å or rather of 2.054(7) to 2.088(7) Å.

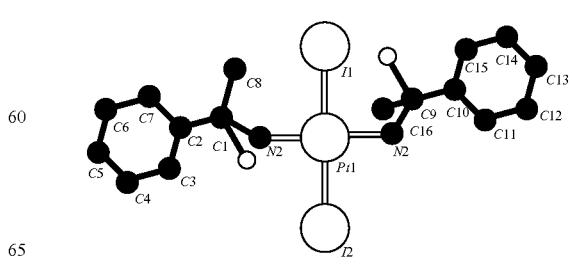

2.3. Second Process Step: Synthesis of (S,S,R$_N$,R$_N$)—PtI(C$_6$H$_4$CHMeNHMe)-(MeHNCHMeC$_6$H$_5$) (2d)

Fortunately, it turned out in the context of the present invention that apart from primary amines, which are relatively sterically undemanding, also amines, which are more sterically demanding, such as secondary amines, can be reacted with the platinum-iodine precursor obtained according to the invention to form cycloplatinated amineiodoplatinum(II) complexes.

For synthesizing (S,S,R$_N$,R$_N$)—PtI(C$_6$H$_4$CHMeNHMe)-(MeHNCHMeC$_6$H$_5$) (2d), 1 mmol of the iodoplatinum precursor obtained in the first process step was suspended in 30 ml a methanol/acetone-mixture(1:1 v/v). Subsequently, 4 mmol of (S)—C$_6$H$_4$CHMeNHMe were added and the reaction mixture was heated to reflux for two days. The filtrate contained also metallic platinum and was filtered by using Celite and subsequently evaporated to dryness. The solid was dissolved in methanol. By addition of water, a light yellow precipitate was formed. (S,S,R$_N$,R$_N$)—PtI(C$_6$H$_4$CHMeNHMe)-(MeHNCHMeC$_6$H$_5$) was obtained by re-crystallization from methanol/water. Single crystal x-ray structure analysis showed that the light yellow crystals were S,S,R$_N$,R$_N$-diastereomers. For clarity reasons, only the hydrogen atoms bound to the chiral center and the nitrogen atoms are shown in FIG. 4.

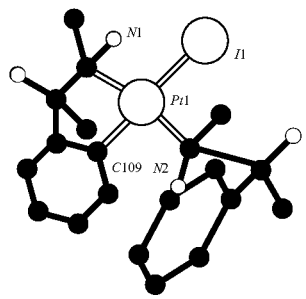

FIG. 4: Molecular Structure of (S,S,R$_N$,R$_N$)—PtI(C$_6$H$_4$CHMeNHMe)-(MeHNCHMeC$_6$H$_5$) (2d) Determined by Single Crystal X-Ray Structure Analysis Selected bond lengths [Å] and bond angles [°] of (S,S,R$_N$,R$_N$)—PtI(C$_6$H$_4$CHMeNHMe)-(MeHNCHMeC$_6$H$_5$) (2d): Pt—N1 2.056(3), Pt—N2 2.071(3), Pt—I1 2.7055(3), Pt—C109 1.987(3), N2-Pt—N1 173.79(11), C109-Pt—I1 170.30(10), C109-Pt—N1 81.11(13), C109-Pt—N2 93.38(13), N1-Pt—I1 89.86(8), N2-Pt—I1 95.80(8); Micro analysis: H: 4.26, C: 36.56, N: 4.74 (calculated), H: 4.20, C: 36.55, N: 4.75 (measured).

3. Third Process Step: Ligand Exchange Reaction

3.1 Synthesis of (S)—PtI(C$_6$H$_4$CHMeNH$_2$)P(C$_6$H$_5$)$_3$ (4a)

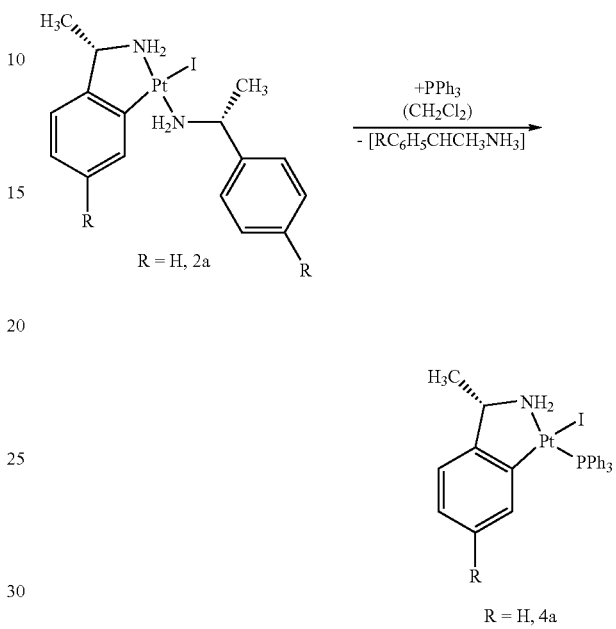

In the context of the present invention, it was found that the monodentate binding amine ligand can easily be varied by a ligand exchange reaction. Thereby, the already large number of compounds preparable according to the invention can further be raised.

For synthesizing (S)—PtI(C$_6$H$_4$CHMeNH$_2$)P(C$_6$H$_5$)$_3$ (4a), the cycloplatinated amineiodoplatinum complex 2a and triphenylphosphane (PPh$_3$) were stirred in a 1:1-ratio in CH$_2$Cl$_2$ for one hour at room temperature. Subsequently, hexane was added, whereupon (S)—PtI(C$_6$H$_4$CHMeNH$_2$)P(C$_6$H$_5$)$_3$ (4a) precipitated, which was filtered off and re-crystallized from an isopropanol/CH$_2$Cl$_2$-mixture.

NMR: $^1$H-NMR (400 MHz, CD$_2$Cl$_2$): δ=1.59 (d, 3H, J=6.84 Hz, CHMe); 4.38 (q, 1H, J=5.12 Hz, CH); 5.29 (br, 1H, NH); 6.04 (br, 1H, NH); 6.24 (m, 1H, Ph); 6.38 (dd, 1H, J=2.80 Hz, J=7.74 Hz, Ph); 6.77 (m, 1H, Ph); 6.94 (m, 1H, Ph); 7.39-7.45 (m, 9H, PPh$_3$); 7.63-7.70 (m, 6H, PPh3) ppm. $^{13}$C-NMR (100.6 MHz, CD$_2$Cl$_2$): δ=25.14 (s, 1C, CH3); 62.67 (s, 1C, CH); 121.10, (s, 1C, Ph); 122.66 (s, 1C, Ph); 124.33 (s, 2C, Ph); 127.71 (d, 6C, JC—P=10.06 Hz, meta-C, PPh3); 130.39 (s, 3C, para-C, PPh$_3$); 134.64 (d, 6C, JC—P=10.06 Hz, ortho-C, PPh$_3$); 132.02 (d, 3C, JC—P=57.35 Hz, ipso-C, PPh$_3$); 142.48 (s, 1C, C6); 155.65 (s, 1C, C1) ppm. $^{31}$P-NMR (121.5 MHz, CD$_2$Cl$_2$): δ=21.17 (t, 1P, JP—Pt=4259.13 Hz, PPh$_3$). $^{195}$Pt-NMR (107.4 MHz, CD$_2$Cl$_2$): δ=−4246.79 (d, 1Pt, JP—Pt=4247.00) ppm. Micro analysis: H: 3.58, C: 44.33, N: 1.99 (calculated), H: 3.68, C: 44.54, N: 2.00 (measured).

The molecular structure of (S)—PtI(C$_6$H$_4$CHMeNH$_2$)P(C$_6$H$_5$)$_3$ (4a) could also be determined by single crystal x-ray structure analysis in the context of the present invention (see FIG. 5). For clarity reasons, also in FIG. 5, only the hydrogen atom bound to the chiral center is shown.

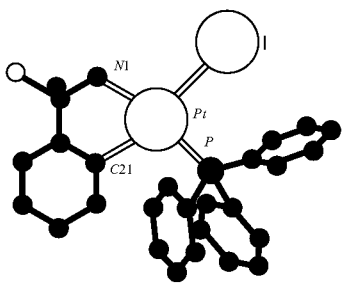

FIG. 5: Molecular Structure of (S)—PtI (C$_6$H$_4$CHMeNH$_2$)P(C$_6$H$_5$)$_3$ (4a) Determined by Single Crystal X-Ray Structure Analysis Selected bond length and angles of (S)—PtI (C$_6$H$_4$CHMeNH$_2$)P(C$_6$H$_5$)$_3$ (4a): Pt—C21 2.041(5), Pt—N1 2.108(5), Pt—P 2.2337(15), Pt—I 2.7008(7) Å, C21-Pt—I 165.54(15), N1-Pt—P 172.43(15)°.

3.2 Synthesis of rac-, (S)— or (R)—PtI(4-R—C$_6$H$_3$CHMeNH$_2$)-(4-CH$_3$—C$_5$H$_5$N) (R=H (5a), Me (5b) or F (5c)

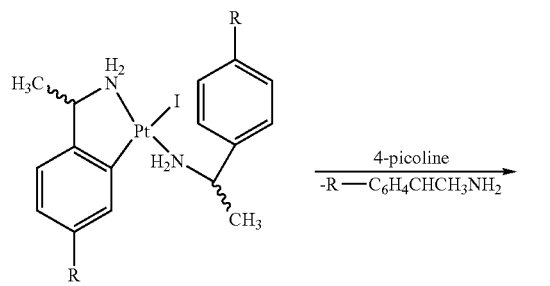

R = H, 2a
R = Me, 2b
R = F, 2c

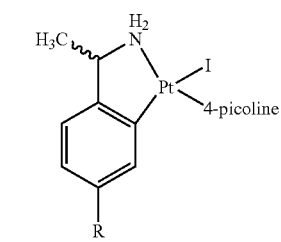

R = H, donor ligand = 4-picoline, 5a
R = CH3, donor ligand = 4-picoline, 5b
R = F, donor ligand = 4-picoline, 5c For synthesizing PtI(4-R—C$_6$H$_3$CHMeNH$_2$)-(4-CH$_3$—C$_5$H$_4$N) (R=H (5a), Me (5b) or F (5c)), one of the cycloplatinated amineiodoplatinum complexes according to the invention 2a, 2b and 2c, respectively, and 4-picoline(4-methyl-pyridine) were stirred in a 1:1-ratio in CH$_2$Cl$_2$ and heated to reflux for two days. A white precipitate was formed, which was filtered off. Yield: 88% in the case of R=H (5a), 79% in the case of R=Me (5b) and 82% in the case of R=F (5c).

The products were analyzed by single crystal x-ray structure analysis, nuclear magnetic resonance (NMR) and micro analysis. Single crystal x-ray structure analysis showed that the products crystallize isomorphous in the tetragonal space group I4$_1$ with two crystallographically independent molecules in the asymmetric unit. For clarity reasons, in the following FIGS. 6 to 8, only one of the two crystallographically independent molecules and only the hydrogen atom bound to the chiral center are shown.

3.2.1 (R)—PtI(C$_6$H$_4$CHMeNH$_2$)-(4-Me-C$_5$H$_4$N) (5a)

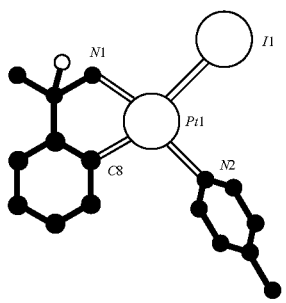

FIG. 6: Molecular Structure of (R)—PtI (C$_6$H$_4$CHMeNH$_2$)-(4-Me-C$_5$H$_4$N) (5a) Determined by Single Crystal X-Ray Structure Analysis (R)—PtI(C$_6$H$_4$CHMeNH$_2$)-(4-Me-C$_5$H$_4$N) (5a): Selected bond lengths [Å] and bond angles [°], parameters of the second molecule are given in square brackets: Pt1-N1 2.056 (13), [2.005(13)], Pt1-N2 2.011(12), [2.024(12)], Pt1-I1 2.6814(15), [2.6912(14)], Pt1-C8 2.010(15), [1.954(15)], N2-Pt1-N1 175.3(5), [176.1(5)], C8-Pt1-I1 174.2(4), [174.7 (4)], N1-Pt1-I1 93.3(4), [93.2(4)], N2-Pt1-I1 91.2(4), [90.6 (4)], C8-Pt1-N1 80.9(5), [81.5(6)], N2-Pt1-C8 94.6(6), [94.7 (6)]; dihedral angle [°] between the coordination plane and pyridine ring: 73.0(5) [82.7(5)]; NMR: $^1$H-NMR (400 MHz, C$_6$D$_6$): δ=0.82 (d, 3H, J=6.60 Hz, CHMe cycloplatinated amine), 1.40 (s, 1H, 4-Me(Py)); 3.40-3.60 (b, 2H, NH$_2$); 4.19 (m, 1H, CH); 6.00-8.76 (m, 7H, Ph, Py) ppm; $^{195}$Pt-NMR (107.4 MHz, C$_6$D$_6$): −3306.29 (s, 1Pt) ppm; Micro analysis: H: 3.20, C: 31.41, N: 5.23 (calculated), H: 3.29, C: 32.31, N: 5.35(measured); melting point: 241° C. (with decomposition).

3.2.2 (S)—PtI(4-Me-C$_6$H$_3$CHMeNH$_2$)-(4-Me-C$_5$H$_4$N) (5b)

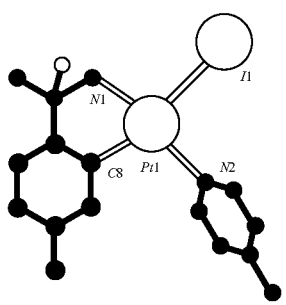

FIG. 7: Molecular Structure of (S)—PtI(4-Me-C$_6$H$_3$CHMeNH$_2$)-(4-Me-C$_5$H$_4$N) (5b) Determined by Single Crystal X-Ray Structure Analysis (S)—PtI(4-Me-C$_6$H$_3$CHMeNH$_2$)-(4-Me-C$_5$H$_4$N) (5b): Selected bond lengths [Å] and bond angles [°], parameters of the second molecule are given in square brackets: Pt1-N1 2.04(2), [2.01(2)], Pt1-N2 1.99(2), [2.09(2)], Pt1-I1 2.708(3), [2.695(3)], Pt1-C8 2.02(3), [1.95(3)], N2-Pt1-N1 173.8(10), [176.7(8)], C8-Pt1-I1 173.2(7), [174.6(8)], N1-Pt1-I1 92.9 (7), [91.6(8)], N2-Pt1-I1 93.3(7), [89.8(6)], C8-Pt1-N1 80.5 (10), [83.9(10)], N2-Pt1-C8 93.3(10), [94.8(10)]; dihedral angle [°] between the coordination plane and pyridine ring: 71.5(10) [72.7(10)]; NMR: $^1$H-NMR (400 MHz, C$_6$D$_6$): δ=0.88 (d, 3H, J=6.60 Hz, CHMe cycloplatinated amine), 1.53 (s, 1H, CHMe), 2.09 (s, 1H, 4-Me(Py)); 3.05, 3.59 (m, 2H, NH$_2$); 4.08 (m, 1H, CH); 6.02-8.38 (m, 7H, Ph, Py) ppm, $^{195}$Pt-NMR (107.4 MHz, C$_6$D$_6$): −3188.05 (s, 1Pt) ppm; Micro analysis: H: 3.49, C: 32.80, N; 5.10 (calculated), H: 3.61, C: 32.77, N: 4.99 (measured); melting point: 218° C. (with decomposition).

3.2.3 (S)—PtI(4-F—C$_6$H$_3$CHMeNH$_2$)-(4-Me-C$_5$H$_4$N) (5c)

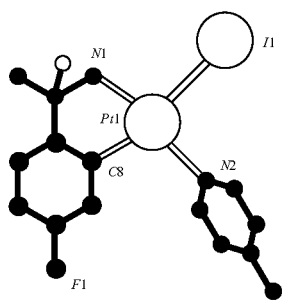

FIG. 8: Molecular Structure of (S)—PtI(4-F—C$_6$H$_3$CHMeNH$_2$)-(4-Me-C$_5$H$_4$N) (5c) Determined by Single Crystal X-Ray Structure Analysis (S)—PtI(4-F—C$_6$H$_3$CHMeNH$_2$)-(4-Me-C$_5$H$_4$N) (5c): Selected bond length [Å] and bond angles [°], parameters of the second molecule are given in square brackets: Pt1-N1 2.050(8), [2.038(8)], Pt1-N2 2.035(8) [2.044(8)] Pt1-I1 2.6981(11) [2.7075(11)], Pt1-C8 1.997(9)[1.996(9)], N2-Pt1-N1 174.5(4) [177.2(4)], C8-Pt1-I1 174.1(3) [173.9 (3)], N1-Pt1-I1 93.4(3) [92.5(3)], N2-Pt1-I1 91.6(3) [90.2 (3)], C8-Pt1-N1 80.6(4) [81.7(4)], C8-Pt1-N2 94.3(5) [95.6 (5)], dihedral angle [°] between the coordination plane and pyridine ring: 70.1(5) [79.2(5)]; NMR: $^1$H-NMR (400 MHz, C$_6$D$_6$): δ=1.32, 1.34 (s, 2H, CHMe, 4-Me(Py)); 2.63, 2.97 (m, 2H, NH$_2$); 4.28 (m, 1H, CH); 6.59-6.69 (m, 7H, Ph, Py) ppm, $^{19}$F-NMR (188.15 Mhz, C$_6$D$_6$): −113.32 (m, 1F, F) ppm, $^{195}$Pt-NMR (107.4 MHz, C$_6$D$_6$): −3376.38 (s, 1Pt) ppm; Micro analysis: H: 2.91, C: 30.39, N: 5.06 (calculated), H: 3.01, C: 30.10, N: 4.98 (measured).

3.3 Synthesis of rac-, (S)— or (R)—[Pt (C$_6$H$_4$CHMeNH$_2$)(C$_{10}$H$_8$N$_2$)] (NO$_3$) (6)

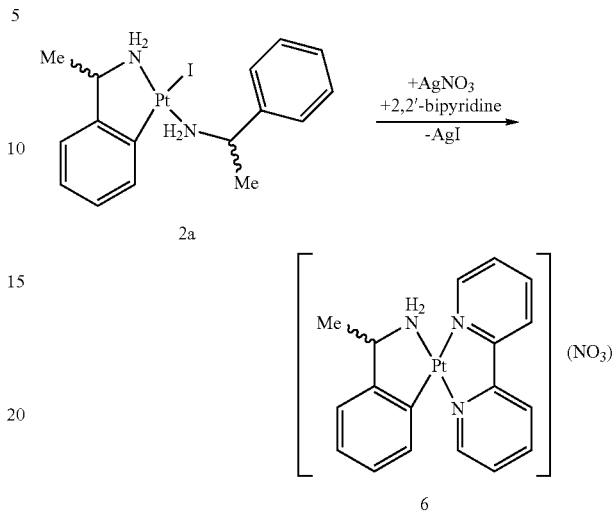

Both, the halogen ligand and the h$^1$-amine can be replaced by a chelating ligand, for example by reaction with the silver salt of acetylacetonate or of a weakly coordinating anion in the presence of a chelating ligand, such as 2,2'bipyridine.

For synthesizing (R)—[Pt(C$_6$H$_4$CHMeNH$_2$)(C$_{10}$H$_8$N$_2$)] (NO$_3$) (6), the cycloplatinated amineiodoplatinum complex according to the invention 2a was dissolved in acetone and an equimolar amount of an aqueous silver nitrate solution was added. Subsequently, one equivalent of 2,2'-bipyridine was added to the reaction mixture and the reaction mixture was stirred over night at room temperature. The solvent was evaporated to dryness and methanol was added. Subsequently, the silver iodide was filtered off by using Celite. The light yellow filtrate was concentrated to dryness. Subsequently, dichlormethane was added. By addition of hexane (R)—[Pt(C$_6$H$_4$CHMeNH$_2$)(2,2'-bipyridine)](NO$_3$).2H$_2$O(6 (.2H$_2$O)) crystallized.

The product was analyzed by single crystal x-ray structure analysis. Single crystal x-ray structure analysis showed that the crystal structure comprises two water molecules per complex molecule. The water molecules are not shown in the following FIG. 9. Furthermore, only the hydrogen atom bound to the chiral center is shown in FIG. 9 for clarity reasons.

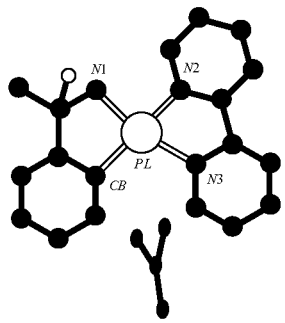

FIG. 9: Molecular Structure of Pt($C_6H_4$CHMeNH$_2$)(2,2'-bipyridin)](NO$_3$).2H$_2$O(6(.2H$_2$O)) Determined by Single Crystal X-Ray Structure Analysis Pt($C_6H_4$CHMeNH$_2$)(2,2'-bipyridin)](NO$_3$). 2H$_2$O(6(.2H$_2$O)): Selected bond lengths [Å] and bond angles [°]: Pt—N1 2.031(6), Pt—N2 2.031(6), Pt—N3 2.050(5), Pt—C8 2.010(6), N2-Pt—N1 98.4(2), C8-Pt—N3 103.1(2), C8-Pt—N1 80.1(2), C8-Pt—N2 174.8(2), N1-Pt—N3 173.4(2), N2-Pt—N3 78.9(2).

4. Anti Tumor Activity (S,S)—PtI($C_6H_4$CHMeNH$_2$)(H$_2$NCHMeC$_6$H$_5$) (2a) and the enantiomer (R,R)—PtI($C_6H_4$CHMeNH$_2$)(H$_2$NCHMeC$_6$H$_5$) were tested on cell lines of the type KG1a (acute myeloid leukemia), LP1 (multiple myeloma) and U266 (multiple myeloma). The complexes had IC50 values between 1 and 2 μM, which is within the clinically practicable concentration range.

The invention claimed is:

1. Process for preparing cycloplatinated platinum(II) complexes, wherein
   in a first process step, at least one halogenoplatinum(II) compound and/or pseudohalogenoplatinum(II) compound is reacted with hydroiodic acid and
   in a second process step, the product of the first process step is reacted with at least one primary or secondary or tertiary amine to form a cycloplatinated amineiodoplatinum(II) complex.

2. Process according to claim 1, characterized in that in the second process step, the product of the first process step is reacted with at least one primary or secondary amine to form a cycloplatinated amineiodoplatinum(II) complex.

3. Process according to claim 1, characterized in that in the second process step, the product of the first process step is reacted with at least one primary amine to form a cycloplatinated amineiodoplatinum(II) complex.

4. Process according to claim 1, characterized in that a primary or secondary or tertiary amine is used, in which the amine group is connected via at least one carbon atom to an aromatic group, which has at least one hydrogen atom in ortho-position relative to the amine group being connected via one or more carbon atoms to the aromatic group.

5. Process according to claim 1 characterized in that a primary or secondary or tertiary amine is used, in which the amine group is connected via at least one chiral carbon atom to an aromatic group, which has at least one hydrogen atom in ortho-position relative to the amine group being connected via one or more carbon atoms to the aromatic group.

6. Process according to claim 1, characterized in that a tetrahalogenoplatinum(II) compound, for example a dihalogenoplatinum(II) compound and/or an alkali tetrahalogenoplatinum(II) compound and/or an ammonium tetrahalogenoplatinum(II) compound, in particular platinum dichloride, platinum dibromide, platinum diiodide, lithium tetrachloroplatinate, sodium tetrachloroplatinate, potassium tetrachloroplatinate, rubidium tetrachloroplatinate, cesium tetrachloroplatinate, ammonium tetrachloroplatinate, lithium tetrabromoplatinate, sodium tetrabromoplatinate, potassium tetrabromoplatinate, rubidium tetrabromoplatinate, cesium tetrabromoplatinate, ammonium tetrabromoplatinate, lithium tetraiodoplatinate, sodium tetraiodoplatinate, potassium tetraiodoplatinate, rubidium tetraiodoplatinate, cesium tetraiodoplatinate, ammonium tetraiodoplatinate, preferably lithium tetrachloroplatinate, sodium tetrachloroplatinate, potassium tetrachloroplatinate and/or ammonium tetrachloroplatinate is used as halogenoplatinum(II) compound, and/or platinum dicyanide and/or a tetracyanoplatinum(II) compound, for example an alkali tetracyanoplatinum(II) compound and/or an ammonium tetra-cyanoplatinum(II) compound, in particular lithium tetra-cyanoplatinate, sodium tetracyanoplatinate, potassium tetracyanoplatinate, rubidium tetracyanoplatinate, cesium tetracyanoplatinate and/or ammonium tetracyanoplatinate is used as pseudohalogenoplatinum(II) compound.

7. Process according to claim 1, characterized in that a primary or secondary or tertiary amine of the general formula:

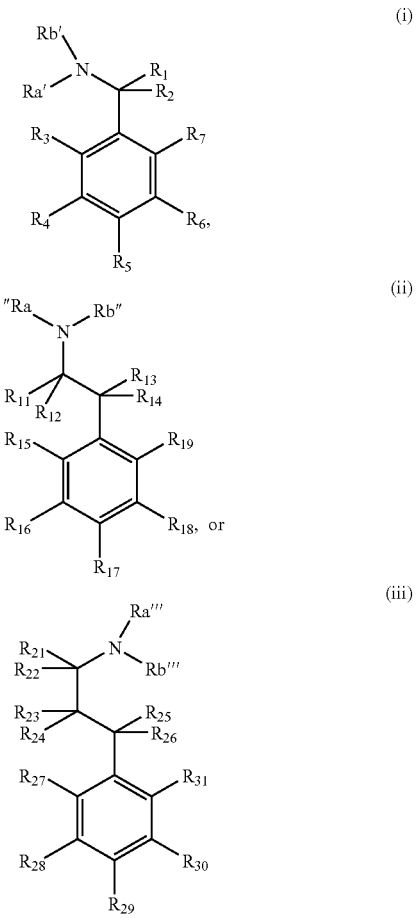

is used, whereas

Ra', Rb', Ra'', Rb'', Ra''', Rb''' each independently of one another represent hydrogen or a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a nitroso group or a silyl group having 1 to 10 carbon atoms, $R_1$-$R_6$, $R_{11}$-$R_{18}$, $R_{21}$-$R_{30}$ each independently of one another represent hydrogen or a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a silyl group having 1 to 10 carbon atoms, and/or $R_1$ or $R_2$ and $R_3$, or $R_{13}$ or $R_{14}$ and $R_{15}$, or $R_{25}$ or $R_{26}$ and $R_{27}$ each represent an unsubstituted or substituted sp3 hybridized carbon atom, whereas $R_1$ or $R_2$ and $R_3$, or $R_{13}$ or $R_{14}$ and $R_{15}$, or $R_{25}$ or $R_{26}$ and $R_{27}$ are interconnected directly or via a further unsubstituted or substituted sp3 hybridized carbon atom in such a manner that a five-membered ring or six-membered ring is formed, and/or $R_{14}$ represents a π-electron and $R_{13}$ and $R_{15}$ each represent an unsubstituted or substituted sp2 hybridized carbon atom, whereas $R_{13}$ and $R_{15}$ are interconnected via a further unsubstituted or substituted sp2 hybridized carbon atom in such a manner that an aromatic six-membered ring is formed, or $R_{26}$ represents a π-electron and $R_{25}$ and $R_{27}$ each represent an unsubstituted or substituted sp2 hybridized carbon atom, whereas $R_{25}$ and $R_{27}$ are interconnected via a further unsubstituted or substituted sp2 hybridized carbon atom in such a manner that an aromatic six-membered ring is formed, and/or $R_{14}$ represents a π-electron and $R_{13}$ represents an unsubstituted or substituted sp2 hybridized carbon atom and $R_{15}$ represents an unsubstituted or substituted nitrogen atom, whereas $R_{13}$ and $R_{15}$ are interconnected in such a manner that an aromatic five-membered ring is formed, or $R_{26}$ represents a π-electron and $R_{25}$ represents an unsubstituted or substituted sp2 hybridized carbon atom and $R_{27}$ represents a nitrogen atom, whereas $R_{25}$ and $R_{27}$ are interconnected in such a manner that an aromatic five-membered ring is formed, and/or $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each represent an unsubstituted or substituted sp2 hybridized carbon atom, whereas $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each are interconnected via two further unsubstituted or substituted sp2 hybridized carbon atoms in such a manner that an aromatic six-membered ring or two aromatic six-membered rings are formed, and $R_7$, $R_{19}$, $R_{31}$ represent hydrogen.

8. Process according to claim 1, characterized in that a primary amine of the general formula:

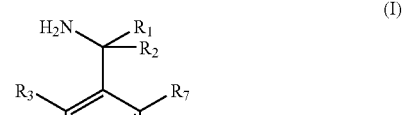

(I)

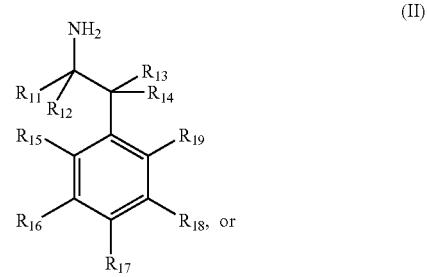

(II)

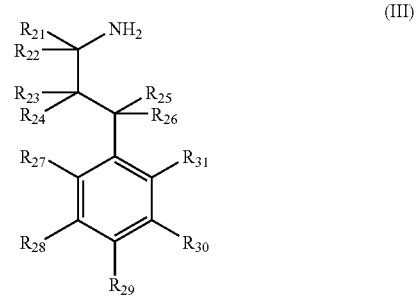

(III)

is used, whereas $R_1$-$R_6$, $R_{11}$-$R_{18}$, $R_{21}$-$R_{30}$ each independently of one another represent hydrogen or a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a silyl group having 1 to 10 carbon atoms, and/or $R_1$ or $R_2$ and $R_3$, or $R_{13}$ or $R_{14}$ and $R_{15}$, or $R_{25}$ or $R_{26}$ and $R_{27}$ each represent an unsubstituted or substituted sp3 hybridized carbon atom, whereas $R_1$ or $R_2$ and $R_3$, or $R_{13}$ or $R_{14}$ and $R_{15}$, or $R_{25}$ or $R_{26}$ and $R_{27}$ are interconnected directly or via a further unsubstituted or substituted sp3 hybridized carbon atom in such a manner that a five-membered ring or six-membered ring is formed, and/or $R_{14}$ represents a π-electron and $R_{13}$ and $R_{15}$ each represent an unsubstituted or substituted sp2 hybridized carbon atom, whereas $R_{13}$ and $R_{15}$ are interconnected via a further unsubstituted or substituted sp2 hybridized carbon atom in such a manner that an aromatic six-membered ring is formed, or $R_{26}$ represents a π-electron and $R_{25}$ and $R_{27}$ each represent an unsubstituted or substituted sp2 hybridized carbon atom, whereas $R_{25}$ and $R_{27}$ are interconnected via a further unsubstituted or substituted sp2 hybridized carbon atom in such a manner that an aromatic six-membered ring is formed, and/or $R_{14}$ represents a π-electron and $R_{13}$ represents an unsubstituted or substituted sp2 hybridized carbon atom and $R_{15}$ represents an unsubstituted or substituted nitrogen atom, whereas $R_{13}$ and $R_{15}$ are interconnected in such a manner that an aromatic five-membered ring is formed, or $R_{26}$ represents a π-electron and $R_{25}$ represents an unsubstituted or substituted sp2 hybridized carbon atom and $R_{27}$ represents a nitrogen atom, whereas $R_{25}$ and $R_{27}$ are interconnected in such a manner that an aromatic five-membered ring is formed, and/or $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each represent an unsubstituted or substituted sp2 hybridized carbon atom, whereas $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each are interconnected via two further unsubstituted or substituted sp2 hybridized carbon atoms in such a manner that an aromatic six-membered ring or two aromatic six-membered rings are formed, and $R_7$, $R_{19}$, $R_{31}$ represent hydrogen.

9. Process according to claim 1, characterized in that the molar ratio of primary amine to the product of the first process step is within a range of $\geq 3:1$ to $\leq 5:1$.

10. Process according to claim 1, characterized in that in the second process step, the product of the first process step is reacted with at least one chiral amine to form a chiral trans-bisaminediiodoplatinum(II) complex and/or to form a chiral cycloplatinated amineiodoplatinum(II) complex.

11. Process according to claim 1, characterized in that the trans-bisaminediiodoplatinum(II) complex and/or the cycloplatinated amineiodoplatinum(II) complex of the second process step is subjected in a third process step to a ligand exchange reaction, in which at least one amine ligand and/or at least one iodo ligand is replaced by another ligand.

12. Process according to claim 11, characterized in that at least one amine ligand or at least one iodo ligand is replaced by a halogen atom, a pseudohalogen, a $C_6F_5$ ligand, an unsubstituted or substituted, linear or branched alkylamine, an unsubstituted or substituted, linear or branched alkenylamine, an unsubstituted or substituted alkynylamine, an unsubstituted or substituted, linear or branched arylalkylamine, a phosphane, a N-heterocycle, or a S-heterocycle, or an amine ligand and an iodo ligand are replaced by a chelate ligand.

13. Chiral trans-bisaminediiodoplatinum(II) complex or chiral cycloplatinated amineiodoplatinum(II) complex obtainable by a process according to claim 1.

14. Cycloplatinated amineiodoplatinum(II) complex of the general formula:

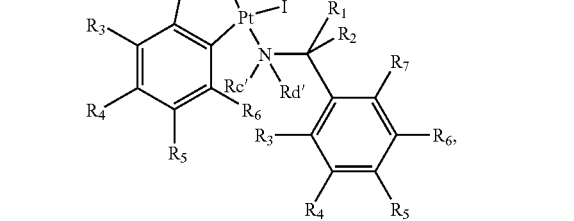

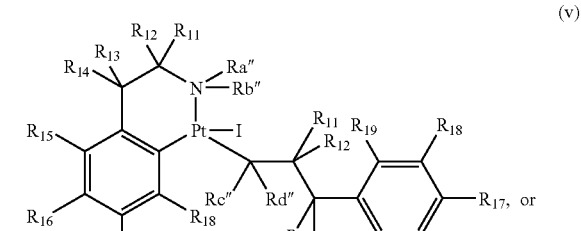

whereas:

Ra'-Rd', Ra"-Rd", Ra'"-Rd'" each independently of one another represent hydrogen or a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a nitroso group or a silyl group having 1 to 10 carbon atoms, $R_1$-$R_6$, $R_{11}$-$R_{18}$, $R_{21}$-$R_{30}$ each independently of one another represent hydrogen or a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a silyl group having 1 to 10 carbon atoms, and/or $R_1$ or $R_2$ and $R_3$, or $R_{13}$ or $R_{14}$ and $R_{15}$, or $R_{25}$ or $R_{26}$ and $R_{27}$ each represent an unsubstituted or substituted sp3 hybridized carbon atom, whereas $R_1$ or $R_2$ and $R_3$, or $R_{13}$ or $R_{14}$ and $R_{15}$, or $R_{25}$ or $R_{26}$ and $R_{27}$ are interconnected directly or via a further unsubstituted o substituted sp3 hybridized carbon atom in such a manner that a five-membered ring or six-membered ring is formed, and/or $R_{14}$ represents a π-electron and $R_{13}$ and $R_{15}$ each represent an unsubstituted or substituted sp2 hybridized carbon atom, whereas $R_{13}$ and $R_{15}$ are interconnected via a further unsubstituted or substituted sp2 hybridized carbon atom in such a manner that an aromatic six-membered ring is formed, or $R_{26}$ represents a π-electron and $R_{25}$ and $R_{27}$ each represent an unsubstituted or substituted sp2 hybridized carbon atom, whereas $R_{25}$ and $R_{27}$ are interconnected via a further unsubstituted or substituted sp2 hybridized carbon atom in such a manner that an aromatic six-membered ring is formed, and/or $R_{14}$ represents a π-electron and $R_{13}$ represents an unsubstituted or substituted sp2 hybridized carbon atom and $R_{15}$ represents an unsubstituted or substituted nitrogen atom, whereas $R_{13}$ and $R_{15}$ are interconnected in such a manner that an aromatic five-membered ring is formed, or $R_{26}$ represents a π-electron and $R_{25}$ represents an unsubstituted or substituted sp2 hybridized carbon atom and $R_{27}$ represents a nitrogen atom, whereas $R_{25}$ and $R_{27}$ are interconnected in such a manner that an aromatic five-membered ring is formed, and/or $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each represent an unsubstituted or substituted sp2 hybridized carbon atom, whereas $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each are interconnected via two further unsubstituted or substituted sp2 hybridized carbon atoms in such a manner that an aromatic six-membered ring or two aromatic six-membered rings are formed, and $R_7$, $R_{19}$, $R_{31}$ represent hydrogen, and $R_1$ is unlike $R_2$.

15. Cycloplatinated amineiodoplatinum(II) complex according to claim 14, characterized in that the complex has the general formula:

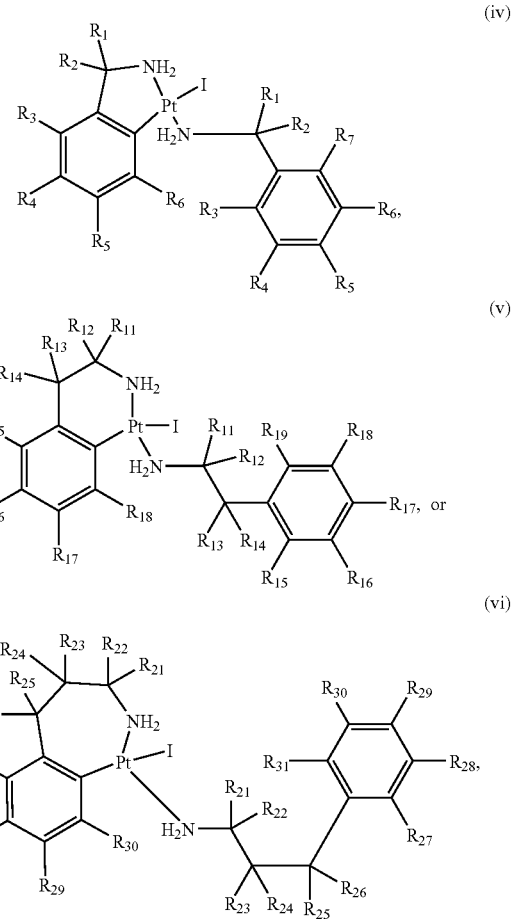

whereas:
$R_1$-$R_6$, $R_{11}$-$R_{18}$, $R_{21}$-$R_{30}$ each independently of one another represent hydrogen or a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a silyl group having 1 to 10 carbon atoms, and/or $R_1$ or $R_2$ and $R_3$, or $R_{13}$ or $R_{14}$ and $R_{15}$, or $R_{25}$ or $R_{26}$ and $R_{27}$ each represent an unsubstituted or substituted sp3 hybridized carbon atom, whereas $R_1$ or $R_2$ and $R_3$, or $R_{13}$ or $R_{14}$ and $R_{15}$, or $R_{25}$ or $R_{26}$ and $R_{27}$ are interconnected directly or via a further unsubstituted or substituted sp3 hybridized carbon atom in such a manner that a five-membered ring or six-membered ring is formed, and/or $R_{14}$ represents a π-electron and $R_{13}$ and $R_{15}$ each represent an unsubstituted or substituted sp2 hybridized carbon atom, whereas $R_{13}$ and $R_{15}$ are interconnected via a further unsubstituted or substituted sp2 hybridized carbon atom in such a manner that an aromatic six-membered ring is formed, or $R_{26}$ represents a π-electron and $R_{25}$ and $R_{27}$ each represent an unsubstituted or substituted sp2 hybridized carbon atom, whereas $R_{25}$ and $R_{27}$ are interconnected via a further unsubstituted or substituted sp2 hybridized carbon atom in such a manner that an aromatic six-membered ring is formed, and/or $R_{14}$ represents a π-electron and $R_{13}$ represents an unsubstituted or substituted sp2 hybridized carbon atom and $R_{15}$ represents an unsubstituted or substituted nitrogen atom, whereas $R_{13}$ and $R_{15}$ are interconnected in such a manner that an aromatic five-membered ring is formed, or $R_{26}$ represents a π-electron and $R_{25}$ represents an unsubstituted or substituted sp2 hybridized carbon atom and $R_{27}$ represents a nitrogen atom, whereas $R_{25}$ and $R_{27}$ are interconnected in such a manner that an aromatic five-membered ring is formed, and/or $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each represent an unsubstituted or substituted sp2 hybridized carbon atom, whereas $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each are interconnected via two further unsubstituted or substituted sp2 hybridized carbon atoms in such a manner that an aromatic six-membered ring or two aromatic six-membered rings are formed, and $R_7$, $R_{19}$, $R_{31}$ represent hydrogen, and $R_1$ is unlike $R_2$.

16. Cycloplatinated platinum(II) complex of the general formula:

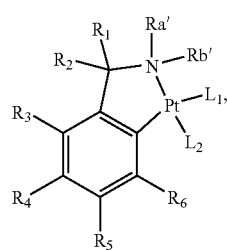

(x)

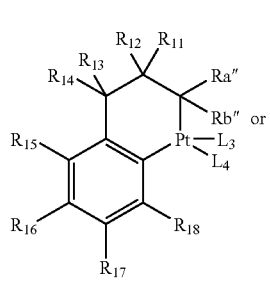

(xi)

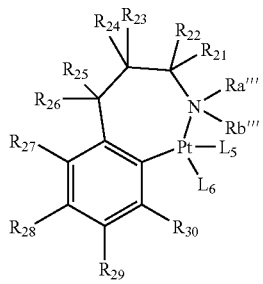

(xii)

whereas:

Ra', Rb', Ra'', Rb'', Ra''', Rb''' each independently of one another represent hydrogen or a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a nitroso group or a silyl group having 1 to 10 carbon atoms, $R_1$-$R_6$, $R_{11}$-$R_{18}$, $R_{21}$-$R_{30}$ each independently of one another represent hydrogen or a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a silyl group having 1 to 10 carbon atoms, and/or $R_1$ or $R_2$ and $R_3$, or $R_{13}$ or $R_{14}$ and $R_{15}$, or $R_{25}$ or $R_{26}$ and $R_{27}$ each represent an unsubstituted or substituted sp3 hybridized carbon atom, whereas $R_1$ or $R_2$ and $R_3$, or $R_{13}$ or $R_{14}$ and $R_{15}$, or $R_{25}$ or $R_{26}$ and $R_{27}$ are interconnected directly or via a further unsubstituted or substituted sp3 hybridized carbon atom in such a manner that a five-membered ring or six-membered ring is formed, and/or $R_{14}$ represents a π-electron and $R_{13}$ and $R_{15}$ each represent an unsubstituted or substituted sp2 hybridized carbon atom, whereas $R_{13}$ and $R_{15}$ are interconnected via a further unsubstituted or substituted sp2 hybridized carbon atom in such a manner that an aromatic six-membered ring is formed, or $R_{26}$ represents a π-electron and $R_{25}$ and $R_{27}$ each represent an unsubstituted or substituted sp2 hybridized carbon atom, whereas $R_{25}$ and $R_{27}$ are interconnected via a further unsubstituted or substituted sp2 hybridized carbon atom in such a manner that an aromatic six-membered ring is formed, and/or $R_{14}$ represents a π-electron and $R_{13}$ represents an unsubstituted or substituted sp2 hybridized carbon atom and $R_{15}$ represents an unsubstituted or substituted nitrogen atom, whereas $R_{13}$ and $R_{15}$ are interconnected in such a manner that an aromatic five-membered ring is formed, or $R_{26}$ represents a π-electron and $R_{25}$ represents an unsubstituted or substituted sp2 hybridized carbon atom and $R_{27}$ represents a nitrogen atom, whereas $R_{25}$ and $R_{27}$ are interconnected in such a manner that an aromatic five-membered ring is formed, and/or $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each represent an unsubstituted or substituted sp2 hybridized carbon atom, whereas $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each are interconnected via two further unsubstituted or substituted sp2 hybridized carbon atoms in such a manner that an aromatic six-membered ring or two aromatic six-membered rings are formed, and $R_1$ unlike $R_2$ ist, and $L_1$-$L_6$ each independently of one another represent a halogen atom, a pseudohalogen, a $C_6F_5$ ligand, an unsubstituted or substituted, linear or branched alkylamine, an unsubstituted or substituted, linear or branched alkenylamine, an unsubstituted or substituted alkynylamine, an unsubstituted or substituted, linear or branched arylalkylamine, a phosphane, a N-heterocycle, or a S-heterocycle, or $L_1$ and $L_2$, or $L_3$ and $L_4$, or $L_5$ and $L_6$ represent a bis(dialkylphosphino)alkane, bis(diphenylphosphino)alkane, bis(dialkylphosphino)alkene, bis(diphenylphosphino)alkene, an alkylene diamine, an oxalate, 2,2'-bis(diphenylphosphino)-1,1'-binaphthyl (BINAP), ethanolamine(2-amineoethanol), thioethanolamine(2-aminoethanethiol), 1,1'-bis(diphenyl)phosphinoferrocene, 2-piperidylmethanol, glycerine, glycolic acid, 1,2-diaminocyclohexane, malonic acid, tetramethylethylenediamine, ethylenediaminetetraacetic acid, N,N'-ribavirin (1-beta-D-ribofuranosyl-1,2,4-triazol-3-carboxamide), acetylacetonate or 2,2'-bipyridine.

17. Cycloplatinated platinum(II) complex of the general formula:

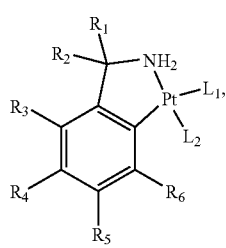

(X)

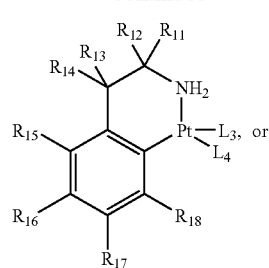

(XI)

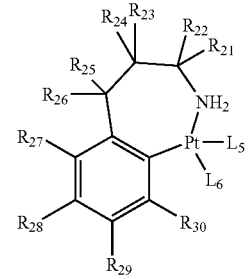

(XII)

whereas:

$R_1$-$R_6$, $R_{11}$-$R_{18}$, $R_{21}$-$R_{30}$ each independently of one another represent hydrogen or a substituted or unsubstituted, halogenated or non-halogenated, linear or branched or cyclic alkyl group or heteroalkyl group having 1 to 10 carbon atoms or a substituted or unsubstituted alkenyl group or alkynyl group having 2 to 10 carbon atoms or a substituted or unsubstituted, halogenated or non-halogenated aryl group or heteroaryl group having 4 to 20 carbon atoms or an aralkyl group or alkaryl group or heteroaralkyl group or heteroalkaryl group having 5 to 20 carbon atoms or a hydroxyl group or a substituted or unsubstituted, linear or branched alkoxy group having 1 to 10 carbon atoms or a substituted or unsubstituted aryloxy group or heteroaryloxy group having 4 to 20 carbon atoms or a formyl group or a substituted or unsubstituted, linear or branched acyl group having 1 to 10 carbon atoms or a carboxylic acid group or a carboxylic ester group having 1 to 10 carbon atoms or a halogen atom or a substituted or unsubstituted sulfonyl group or a substituted or unsubstituted, linear or branched or cyclic amide group having 1 to 10 carbon atoms or a silyl group having 1 to 10 carbon atoms, and/or $R_1$ or $R_2$ and $R_3$, or $R_{13}$ or $R_{14}$ and $R_{15}$, or $R_{25}$ or $R_{26}$ and $R_{27}$ each represent an unsubstituted or substituted sp3 hybridized carbon atom, whereas $R_1$ or $R_2$ and $R_3$, or $R_{13}$ or $R_{14}$ and $R_{15}$, or $R_{25}$ or $R_{26}$ and $R_{27}$ are interconnected directly or via a further unsubstituted or substituted sp3 hybridized carbon atom in such a manner that a five-membered ring or six-membered ring is formed, and/or $R_{14}$ represents a π-electron and $R_{13}$ and $R_{15}$ each represent an unsubstituted or substituted sp2 hybridized carbon atom, whereas $R_{13}$ and $R_{15}$ are interconnected via a further unsubstituted or substituted sp2 hybridized carbon atom in such a manner that an aromatic six-membered ring is formed, or $R_{26}$ represents a π-electron and $R_{25}$ and $R_{27}$ each represent an unsubstituted or substituted sp2 hybridized carbon atom, whereas $R_{25}$ and $R_{27}$ are interconnected via a further unsubstituted or substituted sp2 hybridized carbon atom in such a manner that an aromatic six-membered ring is formed, and/or $R_{14}$ represents a π-electron and $R_{13}$ represents an unsubstituted or substituted sp2 hybridized carbon atom and $R_{15}$ represents an unsubstituted or substituted nitrogen atom, whereas $R_{13}$ and $R_{15}$ are interconnected in such a manner that an aromatic five-membered ring is formed, or $R_{26}$ represents a π-electron and $R_{25}$ represents an unsubstituted or substituted sp2 hybridized carbon atom and $R_{27}$ represents a nitrogen atom, whereas $R_{25}$ and $R_{27}$ are interconnected in such a manner that an aromatic five-membered ring is formed, and/or $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each represent an unsubstituted or substituted sp2 hybridized carbon atom, whereas $R_3$ and $R_4$ and/or $R_5$ and $R_6$ or $R_4$ and $R_5$, or $R_{15}$ and $R_{16}$ and/or $R_{17}$ and $R_{18}$ or $R_{16}$ and $R_{17}$, or $R_{27}$ and $R_{28}$ and/or $R_{29}$ and $R_{30}$ or $R_{28}$ and $R_{29}$ each are interconnected via two further unsubstituted or substituted sp2 hybridized carbon atoms in such a manner that an aromatic six-membered ring or two aromatic six-membered rings are formed, and $R_1$ unlike $R_2$ ist, and $L_1$-$L_6$ each independently of one another represent a halogen atom or a pseudohalogen or a $C_6F_5$ ligand or an unsubstituted or substituted, linear or branched alkylamine or an unsubstituted or substituted, linear or branched alkenylamine or an unsubstituted or substituted alkynylamine or an unsubstituted or substituted, linear or branched arylalkylamine or a phosphane or a N-heterocycle or a S-heterocycle, or $L_1$ and $L_2$, or $L_3$ and $L_4$, or $L_5$ and $L_6$ represent a bis(dialkylphosphino)alkane, bis(diphenylphosphino)alkane, bis(dialkylphosphino)alkene, bis(diphenyl-phosphino)alkene, an alkylene diamine, an oxalate, 2,2'-bis(diphenylphosphino)-1,1'-binaphthyl (BINAP), ethanolamine(2-amineoethanol), thioethanolamine(2-aminoethanethiol), 1,1'-bis(diphenyl)phosphinoferrocene, 2-piperidylmethanol, glycerine, glycolic acid, 1,2-diaminocyclohexane, malonic acid, tetramethylethylenediamine, ethylenediaminetetraacetic acid, N,N'-ribavirin (1-beta-D-ribofuranosyl-1,2,4-triazol-3-carboxamide), acetylacetonate or 2,2'-bipyridine.

18. Platinum complex according to claim 14, characterized in that $R_1$ is unlike $R_2$, or $R_{11}$ is unlike $R_{12}$ and/or $R_{13}$ is unlike $R_{14}$, or $R_{21}$ is unlike $R_{22}$ and/or $R_{23}$ is unlike $R_{24}$ and/or $R_{25}$ is unlike $R_{26}$.

\* \* \* \* \*